(12) United States Patent
Pomerantz et al.

(10) Patent No.: US 6,326,166 B1
(45) Date of Patent: Dec. 4, 2001

(54) CHIMERIC DNA-BINDING PROTEINS

(75) Inventors: Joel L. Pomerantz, Cambridge; Phillip A. Sharp; Carl O. Pabo, both of Newton, all of MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 08/973,131

(22) PCT Filed: Dec. 29, 1995

(86) PCT No.: PCT/US95/16982

§ 371 Date: Mar. 16, 1998

§ 102(e) Date: Mar. 16, 1998

(87) PCT Pub. No.: WO96/20951

PCT Pub. Date: Jul. 11, 1996

(51) Int. Cl.[7] .................................................. C12P 21/02

(52) U.S. Cl. .................. 435/69.1; 435/320.1; 435/455; 435/325; 435/91.53; 800/8; 514/44; 536/23.1

(58) Field of Search .................................. 536/23.1, 23.4; 435/69.1, 320.1, 325, 252.3–252.33, 455, 91.53; 514/44; 800/8

(56) References Cited

U.S. PATENT DOCUMENTS

| | | | |
|---|---|---|---|
| 5,283,173 | 2/1994 | Fields et al. | 435/6 |
| 5,464,758 | 11/1995 | Gossen et al. | 435/69.1 |
| 5,869,337 | 2/1999 | Crabtree et al. | 435/372.3 |

FOREIGN PATENT DOCUMENTS

94/18317 * 8/1994 (WO).

OTHER PUBLICATIONS

Dictionary of Biochemistry and Molecular Biology, 1989, Stenesh, John Wiley & Sons, New York, p. 273.*
Attar, R. and Gilman, M., "Expression Cloning of a Novel Zinc Finger Protein That Binds to the c–fos Serum Response Element," *Moll. Cell. Biol.,* 12:2432–2443 (1992).
Aurora, R. and Herr, W., "Segments of the POU domain influence on another's DNA binding specificity", *Mol. Cell. Biol.,* 12:455 (1992).
Chiu, M. et al., "RAPT1, a mammalian homolog of yeast Tor, interacts with FKBP12/rapamycin complex", *Proc. Natl. Acad. Sci.,* 91:12574–12578 (1994).
Choo, Y. et al., "In vivo repression by a site–specific DNA–binding protein designed against and oncogenic sequence", *Nature,* 372:642–645 (1994).
Choo, Y. et al., "Selection of DNA binding sites for zinc fingers using rationally randomized DNA reveals coded interactions", *Proc. Natl. Acad. Sci. USA,* 91:11168–11172 (1994).

Choo, Y. et al., "Toward a code for the interactions of zinc fingers with DNA: Selection of randoized fingers displayed on phage", *Proc. Natl. Acad. Sci. USA,* 91:11163–11167 (1994).
Desjarlais and Berg, "Use of a Zinc–Finger Concensus Sequence Framework and Specificity Rules to Design Specific DNA Binding Proteins", *Proc. Natl. Acad. Sci.,* 90:2256–2260 (1993).
Clackson, T. and Wells, J., "In vitro selection from protein and peptide libraries", *Trends Biotech.,* 12:173–184 (1994).
Fairall, L. et al., The crystal structure of a two zinc–finger peptide reveals an extension of the rules for zinc–finger/DNA recognition, *Nature,* 366:483–487 (1993).
Frankel et al., "Fingering Too Many Proteins", *Cell,* 53:675 (1988).
Gashler, A. et al., "A Novel Repression Module, an Extensive Activation Domain, and a Bipartite Nuclear Localization Signal Defined in the Immediate–Early Transcription Factor Egr 1", *Mol. Cell. Biol.,* 13:4556–4571 (1993).
Grueneberg, D. et al., "Human and Drosophila Homeodomain Proteins That Enhance the DNA–Binding Activity of Serum Response Factor", *Science,* 257:1089–1095 (1992).
Jacobs, G., "Determination of the base recognition positions of zinc fingers from sequence analysis", *EMBO Journal,* 11:4507–4517 (1992).
Jamieson, Andrew C. et al., "In Vitro Selection of Zinc Fingers with Altered DNA–Binding Specificity", *Biochemistry,* 33(19):5689–5695 (1994).
Kim and Chandrasegaran, "Chimeric Restriction Endonuclease", *Proc. Natl. Acad. Sci.,* 91:883–887 (1994).
Klemm, Juli D. et al., "Crystal Structure of the Oct–1 POU Domain Bound to an Octamer Site: DNA Recognition with Tethered DNA–Binding Molecules", *Cell,* 77:21–32 (1994).
Klevit, R., "Recognition of DNA by $Cys_2,His_2$ Zinc Fingers", *Science,* 253:1367,1393 (1991).
Kordower, J. et al., "The aged monkey basal forebrain: Rescue and sprouting of axotomized basal forebrain neurons after grafts of encapsulated cells secreting human nerve growth factor", *Proc. Natl. Acad. Sci. USA,* 91:10898–10902 (1994).
Laughon, Alan "DNA Binding Specificity of Homeodomains†", *Biochemistry,* 30(48):11357–11367 (1991).
Li, L. et al., "Functional domains in Fok I restriction endonuclease", *Proc. Natl. Acad. Sci. USA,* 89:4275–4279 (1992).

(List continued on next page.)

Primary Examiner—James Martinell
(74) *Attorney, Agent, or Firm*—Matthew P. Vincent; Ropes & Gray, LLP

(57) ABSTRACT

Chineric proteins containing composite DNA-binding regions are disclosed together with DNA constructs encoding them, compositions containing them and applications in which they are useful.

60 Claims, 7 Drawing Sheets

OTHER PUBLICATIONS

Margolin et al., "Kruppel–associated boxes are potent transcriptional repression domains", *Proc. Natl. Acad. Sci.*, 91:4509–4513 (1994).

Miller, J. et al., "Repetitive zinc–binding domains in the protein transcription factor IIIA from Xenopus oocytes", *EMBO Journal*, 4:1609–1614 (1985).

Murre, C. and Baltimore, D., "The Helix–Loop–Helix Motif: Structure and Function", *Transcriptional Regulation*, Cold Spring Harbor Laboratory Press, pp. 861–878 (1992).

Natesan, S. and Gilman, M., "YY1 Facilitates the Association of Serum Response Factor with the c–fos Serum Response Element", *Moll. Cell. Biol.*, 15:5975–5982 (1995).

Park, Changmoon et al., "Design Superiority of Palindromic DNA Sites for Site–Specific Recognition of Proteins: Tests Using Protein Stitchery", *Proc. Natl. Acad. Sci.*, 90:4892–4896 (1993).

Park, Changmoon et al., "Protein Stitchery: Design of a Protein for Selective Binding too a Specific DNA Sequence", *Proc. Natl. Acad. Sci.*, 89:9094–9096–(1992).

Pavletich and Pabo, "Crystal structure of a Five–Finger GLI–DNA Complex: New perspectives on Zinc Finger", *Science*, 261:1701–1707 (1993).

Pavletich and Pabo, "Zinc Finger–DNA Recognition: Crystal Structure of a Zif268–DNA Complex at 2.1 Å", *Research Articles*, 809–817 (1991).

Pollock, R. et al., "A sensitive method for the determination of protein–DNA binding specificities", *Nucleic Acids Research*, 18:6197–6204 (1990).

Pomerantz et al., "Analysis of homeodoman function by structure–based design of a transcription factor", *Proc. Natl. Acad. Sci.*, 92:9752–9756 (1995).

Pomerantz and Sharp, "Homeodomain Determinants of Major Groove Recognition", *Biochemistry*, 33(36):10851–10858 (1994).

Pomerantz et al., "Recognition of the surface of a homeodomain protein", *Genes and Developement*, 6:2047–2057 (1992).

Pomerantz et al., "Structure–Based Design of Transcription Factors", *Science*, 267:93–96 (1995).

Pomerantz et al., "Structure–Based Design of Transcription Factors with Novel DNA–Binding Specificities", *J. Cellular Biochemistry Supplement*, 21A:382 No. C6–232 (1995).

Rebar and Pabo, "Zinc Finger Phage: Affinity Selection of Fingers with New DNA–Binding Specificities", *Science*, 262:671–673 (1994).

Rosenfeld, M., "POU–domain transcription factors: pou–er–ful developmental regulators", *Genes & Dev.*, 5:897–907 (1991).

Scott, M. et al., "The structure and function of the homeodomain", *Biochimica et Biophysica Acta*, 98925–48 (1989).

Spencer, D. et al., "Controlling Signal Transduction with Synthetic Ligands", *Sci.*, 262:1019–1024 (1993).

Stark, M. and Johnson, A., "Interaction between two homeodomain protein is specified by a short C–terminal tail", *Nature*, 371:429–432 (1994).

Stemmer, W., "Rapid evolution of a protein in vitro by DNA shuffling", *Nature*, 370:389–391 (1994).

Sturm, R. et al., "The ubiquitous octamer–binding protein Oct–1 contains a POU domain with a homeo box subdomain", *Genes & Dev.*, 2:1582–1599 (1988).

Suckow, Manfred et al., "Creating New DNA Binding Specificites in the Yeast Transcriptional Activator GCN4 by Combining Selected Amino Acid Substitutions", *Nucleic Acids Research*, 22(12):2198–2208 (1994).

Thiesen et al. "The Krab Domain, A Transcriptional Silencer Present In More Than Hundred Human Kruppel–Type Zinc Finger Proteins", *Experimental Hematology*, 23(8):779 No. C6–232 (1995).

Verrijizer, C. Peter et al., "The DNA–Binding Specificity of the BiPartite POU Domain and Its Subdomains", *The EMBO Journal*, 11(13):4993–5003 (1992).

Verrijizer, P. et al., "The Oct–1 POU domain mediates interaction between Oct–1 and other POU proteins", *Mol. Cell. Biol.*, 12:542 (1992).

Wang, Yaolin et al., "A Regulatory System For Use in Gene Transfer", *Proc. Natl. Acad. Sci.*, USA, 91:8180–8184 (1994).

Wharton and Ptashne, "Changing the DNA–Binding Specificity of a Repressor by Redesigning an α–Helix"*Nature*, 316:601–605 (1985).

Wu, H. et al., "Building zinc fingers by selection: Toward a therapeutic application", *Proc. Natl. Acad.Sci.* USA, 92:344–348 (1995).

Youderain, Phillip et al., "Changing the DNA–Binding Specificity of a Repressor", *Cell*, 35:777–783 (1983).

Brugnera, E. et al., "POU–specific domain of Oct–2 factor confers 'octamer' motif DNA binding specificity on heterologous Antennapedia homeodomain", *FEBS*, 314:361–65 (1992).

Harrison, S., "A structural taxonomy of DNA–binding domains", *Nature*, 353:715–19 (1991).

Mitchell, P., et al., "Transcriptional Regulation in Mammalian Cells by Sequence–Specific DNA Binding Proteins", *Science*, 245:371–78 (1989).

Schultz, P. G., "The Interplay Between Chemistry and Biology in the Design of Enzymatic Catalysts", *Science*, 240:426–33 (1988).

\* cited by examiner

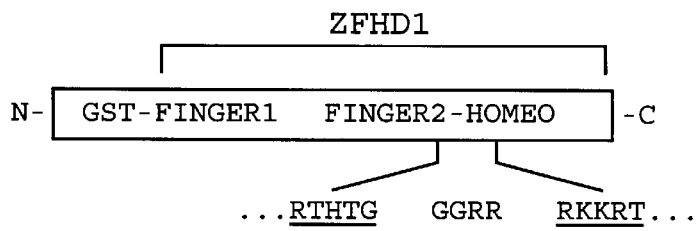

Fig. 1A

```
GTTTGGCACCTGACTAATTTAAGGAG
         GCGTTAATTAAGGGAGGTAAGGCCC
       CTCGGCCGTTAATGAGGGGTGTTCG
              TAATTATGGGCGGGATCGAATAGCC
GGCAATAATCAATCCTTTAATTATGG
    GGCCGTACCTCATGAAATTAGGGGCG
             GTTAATTATGGGTAATAATGGTGC
   GTCGGGCTCTGTTAATTATGGGTGG
            GGATAATTACGGGTGGCATTTAGGC
            GATAAATAGGGGCGTCCCATCCCGT
             TAAATTAGGGCTTTAATTACGGTC
  TCATTAGAGTGTTAATGAGATGCGC
TAGTTGCTAATTTGTATTAATTAAAG
        AGTTATTAATTAAGAATGTTAATTA
      GTGTGATAATGAGCTGGTCCGTCCC
        ATATTAAGGCGTAATTCGGACAAGA
```

Fig. 1B

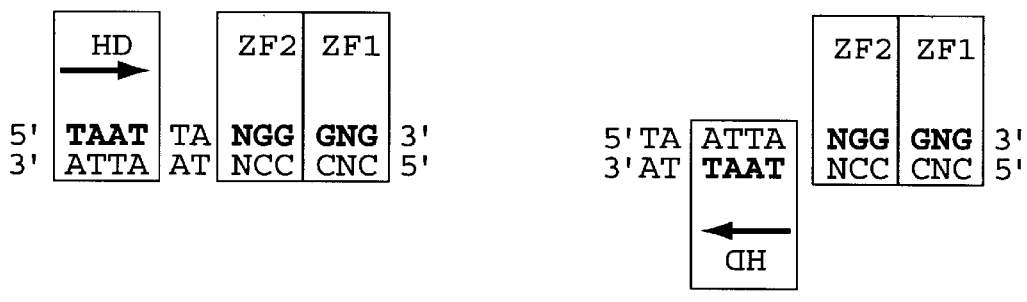

Fig. 1C

```
                         SEQUENCE LISTING

<160> NUMBER OF SEQ ID NOS: 75

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence:
      oligonucleotide used to determine the consensus
      binding sequence of ZFHD1

<400> SEQUENCE: 1
gtttggcacc tgactaattt aaggag                                      26

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence:
      oligonucleotide used to determine the consensus
      binding sequence of ZFHD1

<400> SEQUENCE: 2
gcgttaatta agggaggtaa ggccc                                       25

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence:
      oligonucleotide used to determine the consensus
      binding sequence of ZFHD1

<400> SEQUENCE: 3
ctcggccgtt aatgaggggt gttcg                                       25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence:
      oligonucleotide used to determine the consensus
      binding sequence of ZFHD1

<400> SEQUENCE: 4
taattatggg cgggatcgaa tagcc                                       25

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence:
      oligonucleotide used to determine the consensus
``` binding sequence of ZFHD1

<400> SEQUENCE: 5
ggcaataatc aatcctttaa ttatgg                                       26

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence:
      oligonucleotide used to determine the consensus
      binding sequence of ZFHD1

<400> SEQUENCE: 6
ggccgtacct catgaaatta ggggcg                                       26

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence:
      oligonucleotide used to determine the consensus
      binding sequence of ZFHD1

<400> SEQUENCE: 7
gttaattatg gggtaataat ggtgc                                        25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence:
      oligonucleotide used to determine the consensus
      binding sequence of ZFHD1

<400> SEQUENCE: 8
gtcgggctct gttaattatg ggtgg                                        25

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:
      oligonucleotide used to determine the consensus
      binding sequence of ZFHD1

<400> SEQUENCE: 9
ggataattac gggtggcatt taggc                                        25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence:
      oligonucleotide used to determine the consensus
      binding sequence of ZFHD1

<400> SEQUENCE: 10
gataaatagg ggcgtcccat cccgt                                        25

<210> SEQ ID NO 11
<211> LENGTH: 24

```
<212> TYPE: DNA
<213> ORGANISM: Artificial Sequence
<220> FEATURE:
<223> OTHER INFORMATION: Description of Artificial Sequence:
      oligonucleotide used to determine the consensus
      binding sequence of ZFHD1

<400> SEQUENCE: 11
taaattaggg ctttaattac ggtc                                       24

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence:
      oligonucleotide used to determine the consensus
      binding sequence of ZFHD1

<400> SEQUENCE: 12
tcattagagt gttaatgaga tgcgc                                      25

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence:
      oligonucleotide used to determine the consensus
      binding sequence of ZFHD1

<400> SEQUENCE: 13
tagttgctaa tttgtattaa ttaaag                                     26

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence:
      oligonucleotide used to determine the consensus
      binding sequence of ZFHD1

<400> SEQUENCE: 14
agttattaat taagaatgtt aatta                                      25

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence:
      oligonucleotide used to determine the consensus
      binding sequence of ZFHD1

<400> SEQUENCE: 15
gtgtgataat gagctggtcc gtccc                                      25

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence:
      oligonucleotide used to determine the consensus
      binding sequence of ZFHD1

<400> SEQUENCE: 16
```
atattaaggc gtaattcgga caaga                                              25

<210> SEQ ID NO 17
<211> LENGTH: 12
<212> TYPE: DNA
<213> ORGANISM: Artificial Sequence
<220> FEATURE:
<223> OTHER INFORMATION: Description of Artificial Sequence: consensus
      binding sequence of ZFHD1
<220> FEATURE:
<223> OTHER INFORMATION: "n" represents a, t, c, g or other

<400> SEQUENCE: 17
taattanggg ng                                                            12

<210> SEQ ID NO 18
<211> LENGTH: 12
<212> TYPE: DNA
<213> ORGANISM: Artificial Sequence
<220> FEATURE:
<223> OTHER INFORMATION: Description of Artificial Sequence: hybrid DNA
      site
<220> FEATURE:
<223> OTHER INFORMATION: "n" represents a, t, c, g or other

<400> SEQUENCE: 18
aaatnntggg cg                                                            12

<210> SEQ ID NO 19
<211> LENGTH: 12
<212> TYPE: DNA
<213> ORGANISM: Artificial Sequence
<220> FEATURE:
<223> OTHER INFORMATION: Description of Artificial Sequence: predicted
      binding sequence
<220> FEATURE:
<223> OTHER INFORMATION: "n" represents a, t, c, g or other

<400> SEQUENCE: 19
cgcccannaa at                                                            12

<210> SEQ ID NO 20
<211> LENGTH: 10
<212> TYPE: DNA
<213> ORGANISM: human

<400> SEQUENCE: 20
atgcaaatga                                                               10

<210> SEQ ID NO 21
<211> LENGTH: 12
<212> TYPE: DNA
<213> ORGANISM: Artificial Sequence
<220> FEATURE:
<223> OTHER INFORMATION: Description of Artificial Sequence: hybrid
      binding site

<400> SEQUENCE: 21
taatgatggg cg                                                            12

<210> SEQ ID NO 22
<211> LENGTH: 63
<212> TYPE: DNA
<213> ORGANISM: Artificial Sequence
<220> FEATURE:
<223> OTHER INFORMATION: Description of Artificial Sequence: hybid
      binding site
<220> FEATURE:

<223> OTHER INFORMATION: "n" represents a, t, c, g or other

<400> SEQUENCE: 22
ggctgagtct gaacggatcc nnnnnnnnnn nnnnnnnnnn nnnncctcg agactgagcg    60 tcg                                                                 63

<210> SEQ ID NO 23
<211> LENGTH: 12
<212> TYPE: DNA
<213> ORGANISM: Artificial Sequence
<220> FEATURE:
<223> OTHER INFORMATION: Description of Artificial Sequence: probe

<400> SEQUENCE: 23
tcattatggg cg                                                       12

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: probe

<400> SEQUENCE: 24
cctcgaggtc attatgggcg ctaggtacc                                     29

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence: probe

<400> SEQUENCE: 25
cctcgaggcg cccatcatta ctaggtacc                                     29

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: probe

<400> SEQUENCE: 26
cctcgaggcg cccacgccta ggtacc                                        26

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: probe

<400> SEQUENCE: 27
cctcgaggtc atttgcatac taggtacc                                      28

<210> SEQ ID NO 28
<211> LENGTH: 43
<212> TYPE: DNA
<213> ORGANISM: Artificial Sequence
<220> FEATURE:
<223> OTHER INFORMATION: Description of Artificial Sequence: DNA
      fragment

<400> SEQUENCE: 28

```
ggtaccagta tgcaaatgac tgcagtatgc aaatgacctc gag            43
```

<210> SEQ ID NO 29
<211> LENGTH: 39
<212> TYPE: DNA
<213> ORGANISM: Artificial Sequence
<220> FEATURE:
<223> OTHER INFORMATION: Description of Artificial Sequence: DNA
      fragment

<400> SEQUENCE: 29

```
ggtaccaggc gtgggcgctg caggcgtggg cgcctcgag                 39
```

<210> SEQ ID NO 30
<211> LENGTH: 45
<212> TYPE: DNA
<213> ORGANISM: Artificial Sequence
<220> FEATURE:
<223> OTHER INFORMATION: Description of Artificial Sequence: DNA
      fragment

<400> SEQUENCE: 30

```
ggtaccagta atgatgggcg ctgcagtaat gatgggcgcc tcgag          45
```

<210> SEQ ID NO 31
<211> LENGTH: 18
<212> TYPE: PRT
<213> ORGANISM: human

<400> SEQUENCE: 31

Asn Phe Leu Gln Leu Pro Gln Gln Thr Gln Gly Ala Leu Leu Thr Ser
 1               5                  10                  15

Gln Pro

<210> SEQ ID NO 32
<211> LENGTH: 6
<212> TYPE: PRT
<213> ORGANISM: human

<400> SEQUENCE: 32

Ser Tyr Gly Gln Gln Ser
 1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: encoded
      epitope

<400> SEQUENCE: 33

Tyr Pro Tyr Asp Val Pro Asp Tyr Ala
 1               5

<210> SEQ ID NO 34
<211> LENGTH: 306
<212> TYPE: DNA
<213> ORGANISM: human

<400> SEQUENCE: 34

```
ctgggggcct tgcttggcaa cagcacagac ccagctgtgt tcacagacct ggcatccgtc    60
gacaactccg agtttcagca gctgctgaac cagggcatac ctgtggcccc ccacacaact   120
gagcccatgc tgatggagta ccctgaggct ataactcgcc tagtgacagg ggcccagagg   180
```

```
cccccccgacc cagctcctgc tccactgggg gccccggggc tccccaatgg cctcctttca      240
ggagatgaag acttctcctc cattgcggac atggacttct cagccctgct gagtcagatc      300
agctcc                                                                 306
```

```
<210> SEQ ID NO 35
<211> LENGTH: 72
<212> TYPE: DNA
<213> ORGANISM: Artificial Sequence
<220> FEATURE:
<223> OTHER INFORMATION: Description of Artificial Sequence: DNA
      fragment

<400> SEQUENCE: 35
ctagctaatg atgggcgctc gagtaatgat gggcggtcga ctaatgatgg gcgctcgagt       60
aatgatgggc gt                                                          72
```

```
<210> SEQ ID NO 36
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 36
atgctctaga gaacgcccat atgcttgccc t                                     31
```

```
<210> SEQ ID NO 37
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 37
atgcgcggcc gccgcctgtg tgggtgcgga tgtg                                  34
```

```
<210> SEQ ID NO 38
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 38
atgcgcggcc gcaggaggaa gaaacgcacc agc                                   33
```

```
<210> SEQ ID NO 39
<211> LENGTH: 49
<212> TYPE: DNA
<213> ORGANISM: Artificial Sequence
<220> FEATURE:
<223> OTHER INFORMATION: Description of Artificial Sequence: primer

<400> SEQUENCE: 39
gcatggatcc gattcaacta gtgttgattc ttttttcttt ctggcggcg                  49
```

```
<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 40
```

```
tcagtctaga ggagtgcagg tggaaaccat                                      30
```

<210> SEQ ID NO 41
<211> LENGTH: 40
<212> TYPE: DNA
<213> ORGANISM: Artificial Sequence
<220> FEATURE:
<223> OTHER INFORMATION: Description of Artificial Sequence: primer

<400> SEQUENCE: 41

```
tcagggatcc tcaataacta gtttccagtt ttagaagctc                           40
```

<210> SEQ ID NO 42
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 42

```
actgtctaga gtcagcctgg gggacgag                                        28
```

<210> SEQ ID NO 43
<211> LENGTH: 43
<212> TYPE: DNA
<213> ORGANISM: Artificial Sequence
<220> FEATURE:
<223> OTHER INFORMATION: Description of Artificial Sequence: primer

<400> SEQUENCE: 43

```
gcatggatcc gattcaacta gtcccaccgt actcgtcaat tcc                       43
```

<210> SEQ ID NO 44
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 44

```
atgctctaga ctgggggcct tgcttggcaa c                                    31
```

<210> SEQ ID NO 45
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 45

```
gcatggatcc gctcaactag tggagctgat ctgactcag                            39
```

<210> SEQ ID NO 46
<211> LENGTH: 125
<212> TYPE: DNA
<213> ORGANISM: Artificial Sequence
<220> FEATURE:
<223> OTHER INFORMATION: Description of Artificial Sequence: DNA
      construct
<220> FEATURE:
<221> NAME/KEY: CDS
<222> LOCATION: (12)..(116)

<400> SEQUENCE: 46

```
ccgcggccac c atg ctc gac cct aag aag aag aga aag gta ctc gag ggc      50
             Met Leu Asp Pro Lys Lys Lys Arg Lys Val Leu Glu Gly
```

```
                    1               5                   10
gtg cag gtg gag ctt cta aaa ctg gaa gtc gac tat ccg tac gac gta        98
Val Gln Val Glu Leu Leu Lys Leu Glu Val Asp Tyr Pro Tyr Asp Val
     15                  20                  25 cca gac tac gca ctc gac taagaattc                                     125
Pro Asp Tyr Ala Leu Asp
 30              35
```

<210> SEQ ID NO 47
<211> LENGTH: 35
<212> TYPE: PRT
<213> ORGANISM: Artificial Sequence

<400> SEQUENCE: 47

```
Met Leu Asp Pro Lys Lys Lys Arg Lys Val Leu Glu Gly Val Gln Val
 1               5                   10                  15

Glu Leu Leu Lys Leu Glu Val Asp Tyr Pro Tyr Asp Val Pro Asp Tyr
            20                  25                  30

Ala Leu Asp
        35
```

<210> SEQ ID NO 48
<211> LENGTH: 32
<212> TYPE: DNA
<213> ORGANISM: human
<220> FEATURE:
<221> NAME/KEY: CDS
<222> LOCATION: (6)..(32)

<400> SEQUENCE: 48

```
cgagt ctc gag ctt gga acc gga cct gcc gcc                              32
      Leu Glu Leu Gly Thr Gly Pro Ala Ala
        1               5
```

<210> SEQ ID NO 49
<211> LENGTH: 9
<212> TYPE: PRT
<213> ORGANISM: human

<400> SEQUENCE: 49

```
Leu Glu Leu Gly Thr Gly Pro Ala Ala
 1               5
```

<210> SEQ ID NO 50
<211> LENGTH: 32
<212> TYPE: DNA
<213> ORGANISM: human
<220> FEATURE:
<221> NAME/KEY: CDS
<222> LOCATION: (6)..(32)

<400> SEQUENCE: 50

```
cgagt ctc gag gtg agc gag gag ctg atc cga                              32
      Leu Glu Val Ser Glu Glu Leu Ile Arg
        1               5
```

<210> SEQ ID NO 51
<211> LENGTH: 9
<212> TYPE: PRT
<213> ORGANISM: human

<400> SEQUENCE: 51

```
Leu Glu Val Ser Glu Glu Leu Ile Arg
 1               5
```

<210> SEQ ID NO 52
<211> LENGTH: 32
<212> TYPE: DNA
<213> ORGANISM: human
<220> FEATURE:
<221> NAME/KEY: CDS
<222> LOCATION: (6)..(32)

<400> SEQUENCE: 52 cgagt ctc gag gag atg tgg cat gaa ggc ctg         32
      Leu Glu Glu Met Trp His Glu Gly Leu
        1               5

<210> SEQ ID NO 53
<211> LENGTH: 9
<212> TYPE: PRT
<213> ORGANISM: human

<400> SEQUENCE: 53

Leu Glu Glu Met Trp His Glu Gly Leu
  1               5

<210> SEQ ID NO 54
<211> LENGTH: 32
<212> TYPE: DNA
<213> ORGANISM: human
<220> FEATURE:
<221> NAME/KEY: CDS
<222> LOCATION: (1)..(27)

<400> SEQUENCE: 54 att ggc tgg tgc cct ttc tgg gtc gac cgagt         32
Ile Gly Trp Cys Pro Phe Trp Val Asp
  1               5

<210> SEQ ID NO 55
<211> LENGTH: 9
<212> TYPE: PRT
<213> ORGANISM: human

<400> SEQUENCE: 55

Ile Gly Trp Cys Pro Phe Trp Val Asp
  1               5

<210> SEQ ID NO 56
<211> LENGTH: 32
<212> TYPE: DNA
<213> ORGANISM: human
<220> FEATURE:
<221> NAME/KEY: CDS
<222> LOCATION: (1)..(27)

<400> SEQUENCE: 56 ttg gct gtg cca gga aca tat gtc gac cgagt         32
Leu Ala Val Pro Gly Thr Tyr Val Asp
  1               5

<210> SEQ ID NO 57
<211> LENGTH: 9
<212> TYPE: PRT
<213> ORGANISM: human

<400> SEQUENCE: 57

Leu Ala Val Pro Gly Thr Tyr Val Asp
  1               5

```
<210> SEQ ID NO 58
<211> LENGTH: 32
<212> TYPE: DNA
<213> ORGANISM: human
<220> FEATURE:
<221> NAME/KEY: CDS
<222> LOCATION: (1)..(27)

<400> SEQUENCE: 58 ttc cga cga atc tca aag cag gtc gac cgagt                32
Phe Arg Arg Ile Ser Lys Gln Val Asp
  1               5

<210> SEQ ID NO 59
<211> LENGTH: 9
<212> TYPE: PRT
<213> ORGANISM: human

<400> SEQUENCE: 59

Phe Arg Arg Ile Ser Lys Gln Val Asp
  1               5

<210> SEQ ID NO 60
<211> LENGTH: 29
<212> TYPE: DNA
<213> ORGANISM: Artificial Sequence
<220> FEATURE:
<223> OTHER INFORMATION: Description of Artificial Sequence: DNA
      construct
<220> FEATURE:
<221> NAME/KEY: CDS
<222> LOCATION: (6)..(29)

<400> SEQUENCE: 60 cgaca ctc gag gcc ccc ccg acc gat gtc                    29
      Leu Glu Ala Pro Pro Thr Asp Val
        1               5

<210> SEQ ID NO 61
<211> LENGTH: 8
<212> TYPE: PRT
<213> ORGANISM: Artificial Sequence

<400> SEQUENCE: 61

Leu Glu Ala Pro Pro Thr Asp Val
  1               5

<210> SEQ ID NO 62
<211> LENGTH: 26
<212> TYPE: DNA
<213> ORGANISM: Artificial Sequence
<220> FEATURE:
<223> OTHER INFORMATION: Description of Artificial Sequence: DNA
      construct
<220> FEATURE:
<221> NAME/KEY: CDS
<222> LOCATION: (1)..(21)

<400> SEQUENCE: 62 gac gag tac ggt ggg gtc gac tgtcg                        26
Asp Glu Tyr Gly Gly Val Asp
  1               5

<210> SEQ ID NO 63
<211> LENGTH: 7
<212> TYPE: PRT
<213> ORGANISM: Artificial Sequence

<400> SEQUENCE: 63
```

Asp Glu Tyr Gly Gly Val Asp
 1               5

<210> SEQ ID NO 64
<211> LENGTH: 161
<212> TYPE: DNA
<213> ORGANISM: Artificial Sequence
<220> FEATURE:
<223> OTHER INFORMATION: Description of Artificial Sequence: DNA
      construct
<220> FEATURE:
<221> NAME/KEY: CDS
<222> LOCATION: (12)..(152)

<400> SEQUENCE: 64
ccgcggccac c atg ctc gac cct aag aag aag aga aag gta ctc gag gag        50
             Met Leu Asp Pro Lys Lys Lys Arg Lys Val Leu Glu Glu
              1               5                  10 atg tgg cat gaa cga atc tca aag cag gtc gag gcc ccc ccg acc gat        98
Met Trp His Glu Arg Ile Ser Lys Gln Val Glu Ala Pro Pro Thr Asp
 15                  20                  25 gac gag tac ggt ggg gtc gac tat ccg tac gac gta cca gac tac gca       146
Asp Glu Tyr Gly Gly Val Asp Tyr Pro Tyr Asp Val Pro Asp Tyr Ala
 30                  35                  40                  45 ctc gac taagaattc                                                      161
Leu Asp <210> SEQ ID NO 65
<211> LENGTH: 47
<212> TYPE: PRT
<213> ORGANISM: Artificial Sequence

<400> SEQUENCE: 65

Met Leu Asp Pro Lys Lys Lys Arg Lys Val Leu Glu Glu Met Trp His
 1               5                  10                  15

Glu Arg Ile Ser Lys Gln Val Glu Ala Pro Pro Thr Asp Asp Glu Tyr
                20                  25                  30

Gly Gly Val Asp Tyr Pro Tyr Asp Val Pro Asp Tyr Ala Leu Asp
         35                  40                  45

<210> SEQ ID NO 66
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 66
tcagtctaga tgtaacatat gccagaaagc cttc                                   34

<210> SEQ ID NO 67
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 67
tcagtctaga tgcaaggagt gtggaaaaac cttt                                   34

<210> SEQ ID NO 68
<211> LENGTH: 34
<212> TYPE: DNA
<213> ORGANISM: Artificial Sequence

```
<220> FEATURE:
<223> OTHER INFORMATION: Description of Artificial Sequence: primer

<400> SEQUENCE: 68
tcagtctaga tgtcatgagt gtgggaaagc cttt                          34

<210> SEQ ID NO 69
<211> LENGTH: 46
<212> TYPE: DNA
<213> ORGANISM: Artificial Sequence
<220> FEATURE:
<223> OTHER INFORMATION: Description of Artificial Sequence: primer

<400> SEQUENCE: 69
tcagggatcc tcaataacta gtagccagtt tgtctttgtg gtgata            46

<210> SEQ ID NO 70
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 70
tcagtctaga cataagaaag tcctctctag                               30

<210> SEQ ID NO 71
<211> LENGTH: 44
<212> TYPE: DNA
<213> ORGANISM: Artificial Sequence
<220> FEATURE:
<223> OTHER INFORMATION: Description of Artificial Sequence: primer

<400> SEQUENCE: 71
tcagggatcc tctatatcaa ctagtaggct tctcaccaag atgg              44

<210> SEQ ID NO 72
<211> LENGTH: 43
<212> TYPE: DNA
<213> ORGANISM: Artificial Sequence
<220> FEATURE:
<223> OTHER INFORMATION: Description of Artificial Sequence: primer

<400> SEQUENCE: 72
tcagggatcc tctatatcaa ctagtgggct cctcctgact gtg               43

<210> SEQ ID NO 73
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 73
tcagtctaga ggccggagcc tgctggagt                                29

<210> SEQ ID NO 74
<211> LENGTH: 41
<212> TYPE: DNA
<213> ORGANISM: Artificial Sequence
<220> FEATURE:
<223> OTHER INFORMATION: Description of Artificial Sequence: primer

<400> SEQUENCE: 74
tcagggatcc tcaataacta gtgtaggatt tgaggaggga a                  41
```

```
<210> SEQ ID NO 75
<211> LENGTH: 14
<212> TYPE: PRT
<213> ORGANISM: Artificial Sequence
<220> FEATURE:
<223> OTHER INFORMATION: Description of Artificial Sequence: chimeric
      motif

<400> SEQUENCE: 75

Arg Thr His Thr Gly Gly Gly Arg Arg Arg Lys Lys Arg Thr
 1               5                  10
```

CHIMERIC DNA-BINDING PROTEINS

GOVERNMENT SUPPORT

A portion of the work described herein was supported by grants PO1-CA42063, CDR-8803014 and P30-CA14051 from the U.S. Public Health Service/National Institutes of Health, National Science Foundation and National Cancer Institute, respectively. The U.S. Government has certain rights in the invention. A portion of the work described herein was also supported by the Howard Hughes Medical Institute.

BACKGROUND OF THE INVENTION

DNA-binding proteins, such as transcription factors, are critical regulators of gene expression. For example, transcriptional regulatory proteins are known to play a key role in cellular signal transduction pathways which convert extracellular signals into altered gene expression (Curran and Franza, Cell 55:395–397 (1988)). DNA-binding proteins also play critical roles in the control of cell growth and in the expression of viral and bacterial genes. A large number of biological and clinical protocols, including among others, gene therapy, production of biological materials, and biological research, depend on the ability to elicit specific and high-level expression of genes encoding RNAs or proteins of therapeutic, commercial, or experimental value. Such gene expression is dependent on protein-DNA interactions.

Attempts have been made to change the specificity of DNA-binding proteins. Those attempts rely primarily on strategies involving mutagenesis of these proteins at sites important for DNA-recognition (Rebar and Pabo, Science 263:671–673 (1994), Jamieson et al., Biochemistry 33:5689–5695 (1994), Suckow et al., Nucleic Acids Research 22(12):2198–2208 (1994)). This strategy may not be efficient or possible with some DNA-binding domains because of limitations imposed by their three-dimensional structure and mode of docking to DNA. In other cases it may not be sufficient to achieve important objectives discussed below. Therefore, it is desirable to have a strategy which can utilize many different DNA-binding domains and can combine them as required for DNA recognition and gene regulation.

SUMMARY OF THE INVENTION

This, invention pertains to chimeric proteins which contain at least one composite DNA-binding region and possess novel nucleic acid binding specificities. The chimeric proteins recognize nucleotide sequences (DNA or RNA) sparning at least 10 bases and bind with high affinity to oligonucleotides or polynucleotides containing such sequences. (It should be understood that the nucleotide sequences recognized by the chimeric proteins may be RNA or DNA, although for the sake of simplicity, the proteins of this invention are typically referred to as "DNA-binding", and RNA too is understood, if not necessarily mentioned.)

The terms "chimeric" protein and "composite" domain are used to denote a protein or domain containing at least two component portions which are mutually heterologous in the sense that they do not occur together in the same arrangement in nature. More specifically, the component portions are not found in the same continuous polypeptide sequence or molecule in nature, at least not in the same order or orientation or with the same spacing present in the chimeric protein or composite domain.

As discussed in detail below, a variety of component DNA-binding polypeptides known in the art are suitable for adaptation to the practice of this invention. The chimeric proteins contain a composite region comprising two or more component DNA-binding domains, joined together, either directly or through one amino acid or through a short polypeptide (two or more amino acids) to form a continuous polypeptide. Additional domains with desired properties can optionally be included in the chimeric proteins. For example, a chimeric protein of this invention can contain a composite DNA-binding region comprising at least one homeodomain, such as the Oct-1homeodomain, together with a second polypeptide domain which does not occur in nature identically linked to that homeodomain. Alternatively, the composite DNA-binding domain can comprise one or more zinc finger domains such as zinc finger 1 and/or finger 2 of Zif268, together with a second polypeptide domain which does not occur in nature linked to that zinc finger domain(s).

A number of specific examples examined in greater detail below involve chimeric proteins containing a composite DNA-binding region comprising a homeodomain and one or two zinc finger domains. In one embodiment, the chimeric protein is a DNA-binding protein comprising at least one homeodomain, a polypeptide linker and at least one zinc finger domain. Such a chimeric protein is exemplified by a composite DNA-binding region containing zinc finger 1 or zinc finger 2 of Zif268, an amino acid or a short (2–5 amino acid residue) polypeptide, and the Oct-1 homeodomain. Another example is a chimeric protein containing a composite DNA-binding region comprising zinc fingers 1 and 2 of Zif268, a short linker, such as a glycine-glycine-arginine-arginine polypeptide, and the Oct-1 homeodomain. The latter chimeric protein, designated ZFHD1, is described in detail below. Other illustrative composite DNA-binding regions include those comprising the Oct1 POU specific domain (aa 268–343) and its own flexible linker (aa 344–366) fused to the amino terminus of ZFHD1 and ZFHD1 fused at its carboxy terminus to Zif268 fingers 1 and 2 (aa 333–390) via the Oct1 flexible linker.

In other embodiments, the chimeric protein comprises a composite DNA-binding region containing a chimeric zinc finger-basic-helix-loop-helix protein. One such chimeric protein comprises fingers 1 and 2 of Zif268 and the MyoD bHLH region, joined by a polypeptide linker which spans approximately 9.5 Å between the carboxyl-terminal region of finger 2 and the amino-terminal region of the basic region of the bHLH domain.

In another embodiment, the chimeric protein comprises a composite DNA-binding region containing a zinc finger-steroid receptor fusion. One such chimeric protein comprises fingers 1 and 2 of Zif268 and the DNA-binding domains of the glucocorticoid receptor, joined at the carboxyl-terminal region of finger 2 and the amino-terminal region of the DNA-binding domain of the glucocorticoid receptor by a polypeptide linker which spans approximately 7.4 Å.

As will be seen, one may demonstrate experimentally the selectivity of binding of a chimeric protein of this invention for a recognized DNA sequence. One aspect of that specificity is that the chimeric protein is capable of binding to its recognized nucleotide sequence preferentially over binding to constituent portions of that nucleotide sequence or binding to different nucleotide sequences. In that sense, the chimeric proteins display a DNA-binding specificity which is distinct from that of each of the component DNA-binding domains alone; that is, they prefer binding the entire recognized nucleotide sequence over binding to a DNA sequence containing only a portion thereof. That specificity and selectivity means that the practitioner can design composite DNA-binding regions incorporating DNA-binding domains of known nucleotide binding specificities with the knowledge that the composite protein will selectively bind to a corresponding composite nucleotide sequence and will do so preferentially over the constituent nucleotide sequences.

These chimeric proteins selectively bind a nucleotide sequence, which may be DNA or RNA, spanning at least 10 bases, preferably at least 11 bases, and more preferably 12 or more bases. By way of example, one can experimentally demonstrate selective binding for a 12-base pair nudeotide sequence using the illustrative ZFHD1 composite DNA-binding domain. Typically one will obtain binding to the selected DNA sequence with a Kd value of about $10^{-8}$ or better, preferably $10^{-9}$ or better and even more preferably $10^{-10}$ or better. Kd values may be determined by any convenient method. In one such method one conducts a series of conventional DNA binding assays, e.g. gel shift assays, varying the concentration of DNA and determining the DNA concentration which correlates to half-maximal protein binding.

The nucleotide sequence specificity of binding by chimeric proteins of this invention, illustrated by proteins comprising the peptide sequence of ZFHD1, renders them useful in a number of important contexts because their DNA-binding properties are distinct from those of known proteins. Such uses include the selective transcription, repression or inhibition of transcription, marking, and cleavage of a target nucleotide sequence. The chimeric proteins prefer to bind to a specific nucleic acid sequence and, thus, mark, cleave or alter expression of genes linked to or controlled by a nucleotide sequence containing the recognized nucleic acid sequence. Preferably, the chimeric proteins do not to a significant extent bind the DNA bound by the component domains of the composite DNA-binding region, and, thus, do not mark, cleave or alter normal cellular gene expression other than by design.

In one application, the chimeric proteins bind a selected nucleic acid sequence within a DNA or RNA and, as a result, mark or flag the selected DNA or RNA sequence, which can be identified and/or isolated from the DNA using known methods. In this respect, the chimeric proteins act in a manner similar to restriction enzymes, in that they recognize DNA or RNA at a selected nucleic acid sequence, thus marking that sequence where ever it occurs in DNA or RNA with which the chimeric proteins are contacted. Unlike restriction enzymes, chimeric DNA-binding or RNA-binding proteins do not cut or fragment the DNA or RNA at the nucleic adds they recognize. Chimeric proteins used for this purpose can be labelled, e.g., radioactively or with an affinity ligand or epitope tag such as GST, and thus, the location of DNA or RNA to which they bind can be identified easily. Because of the binding specificity of the chimeric proteins, DNA or RNA to which binding occurs must include either the nucleotide sequence which the chimeric proteins have been designed to recognize or the nucleotide sequences recognized by the component DNA-binding domains. Optimally, the chimeric protein will not efficiently recognize the nucleotide sequence recognized by the component DNA-binding domains. Standard methods, such as DNA cloning and sequencing, can be used to determine the nucleotide sequence to which the chimeric protein is bound.

In view of the ability of a composite DNA-binding region to fold and function in an autonomous manner, chimeric proteins of the various embodiments of this invention may further comprise one or more additional domains, including for example a transcription activation domain, a transcription repressing domain, a DNA-cleaving domain, a ligand-binding domain, or a protein-binding domain.

Such a chimeric protein which contains a transcription activation domain constitutes a chimeric transcription factor which is capable of activating the transcription of a gene linked to a DNA sequence recognized (i.e., selectively bound) by the chimeric protein. Various transcription activation domains are known in the art and may be used in chimeric proteins of this invention, including the Herpes Simplex Virus VP16 activation domain and the NF-κB p65 activation domain which are derived from naturally occurring transcription factors. One class of such transcription factors comprise at least one composite DNA-binding region, e.g. one containing at least one homeodomain and at least one zinc finger domain (such as the peptide sequence of ZFHD1), and at least one additional domain capable of activating transcription of a gene linked to a DNA sequence to which the transcription factor can bind. These are illustrated by the ZFHD1-VP16 and ZFHD1-p65 chimeras discussed below.

Chimeric proteins of this invention also include those which are capable of repressing transcription of a target gene linked to a nucleotide sequence to which the chimeric proteins bind. Such a chimeric protein functions as a somewhat classical repressor by binding to a nucleotide sequence and blocking, in whole or part, the otherwise normal functioning of that nucleotide sequence in gene expression, e.g. binding to an endogenous transcription factor. Other chimeric proteins of this invention which are capable of repressing or inhibiting transcription of a target gene linked to a nucleotide sequence to which the chimeric protein binds include chimeric proteins containing a composite DNA-binding region, characteristic of all chimeric proteins of this invention, and an additional domain, such as a KRAB domain or a ssn-6/TUP-1 or Krüppel-family suppressor domain, capable of inhibiting orrepressing the expression of the target gene in a cell. In either case, binding of the chimeric protein to the nucleotide sequence linked to the target gene is associated with decreased transcription of the target gene.

Chimeric proteins of this invention also include those which are capable of cleaving a target DNA or RNA linked to a nucleotide sequence to which the chimeric proteins bind. Such chimeric proteins contain a composite DNA-binding region, characteristic of all chimeric proteins of this invention, and an additional domain, such as a FokI domain, capable of cleaving a nucleic acid molecule. Binding of the chimeric protein to the recognition sequence linked to the target DNA or RNA is associated with cleavage of the target DNA or RNA.

Chimeric proteins of this invention further include those which are capable of binding to another protein molecule, e.g., for use in conducting otherwise conventional two-hybrid experiments. See e.g., Fields and Song, U.S. Pat. No. 5,283,173 (Feb. 1, 1994). In addition to the characteristic composite DNA-binding region, proteins of this embodiment contain an additional domain which is, or may be, capable of binding to another protein, known or unknown. In such experiments, the chimeric protein containing the composite DNA-binding region replaces the GAL4-containing fusion protein in the 2-hybrid system and the nucleotide sequence recognized by our chimeric protein replaces the GAL4 binding sites linked to the reporter gene.

Chimeric protein s of this invention further include those which further contain a ligand-binding domain permitting ligand-regulated manifestation of biological activity. Chimeric DNA-binding proteins of this aspect of the invention can be complexed or "dimerized" with other ligand-binding fusion proteins by the presence of an appropriate dimerizing ligand. Examples of such chimeric proteins include proteins containing a characteristic composite DNA-binding region and a ligand-binding domain such as an immunophilin like FKBP12. The divalent ligand, FK1012, for example, is capable of binding to a chimeric, protein of this invention which also contains one or more FKBP domains and to another FKBP-containing protein, including a fusion protein containing one or more copies of FKBP linked to a transcription activation domain. See Spencer, D. M., et al. 1993. *Science.* 262:1019–1024, and PCT/US94/01617. Cells expressing such fusion proteins are capable of dimerizer-dependent transcription of a target gene linked to a nucleotide sequence to to which the DNA-binding chimera is capable of binding.

This invention further encompasses DNA sequences encoding the chimeric proteins containing a composite DNA-binding region. Such DNA sequences include, among others, those which encode a chimeric protein in which the composite DNA-binding region contains a homeodomain covalently linked to at least one zinc finger domain, exemplified by chimeric proteins containing the peptide sequence of ZFHD1. As should be dear from the preceding discussion, the DNA sequence may encode a chimeric protein which further comprises one or more additional domains including, for instance, a transcription activation domain, a transcription repressing domain, a domain capable of cleaving an oligonucleotide or polynucleotide, a domain capable of binding to another protein, a ligand-binding domain or a domain useful as a detectable label.

This invention further encompasses a eukaryotic expression construct containing a DNA sequence encoding the chimeric protein operably linked to expression control elements such as promoter and enhancer elements permitting expression of the DNA sequence and production of the chimeric protein in eukaryotic cells. One or more of those expression control elements may be inducible, permitting regulated expression of the DNA encoding the chimeric protein. The expression control elements may be tissue-specific or cell-type-specific, permitting preferential or selective expression of the chimeric protein in a cell-type or tissue of particular interest. An example of a eukaryotic expression vector of this invention is the plasmid pCGNN ZFHD1-FKBPX3 (ATCC No. 97399) which is capable of directing the expression in mammalian cells of a fusion protein containing a ZFHD1 composite DNA-binding region linked to three FKBP12 domains, discussed in greater detail below.

Using DNA sequences encoding the chimeric proteins of this invention, and vectors capable of directing their expression in eukaryotic cells, one may genetically engineer cells for a number of important uses. To do so, one first provides an expression vector or construct for directing the expression in a eukaryotic cell of the desired chimeric protein and then introduces the vector DNA into the cells in a manner permitting expression of the introduced DNA in at least a portion of the cells. One may use any of the various methods and materials for introducing DNA into cells for heterologous gene expression, many of which are well known. A variety of such materials are commercially available.

In some cases the target gene and its linked nucleotide sequence specifically recognized by the chimeric protein are endogenous to, or otherwise already present in, the engineered cells. In other cases, DNA comprising the target gene and/or the recognized DNA sequence is not endogenous to the cells and is also introduced into the cells.

The various DNA constructs may be introduced into cells maintained in culture or may be administered to whole organisms, including humans and other animals, for introduction into cells in vivo. A variety of methods and materials to effect the delivery of DNA into animals for the introduction into cells are known in the art.

By these methods, one may genetically engineer cells, whether in culture or in vivo, to express a chimeric protein capable of binding to a DNA sequence linked to a target gene within the cells and marking the DNA sequence, activating transcription of the target gene, repressing transcription of the target gene, cleaving the target gene, etc. Expression of the chimeric protein may be inducible, cell-type-specific, etc., and the biological effect of the chimeric protein may be ligand-dependent, all as previously mentioned.

This invention further encompasses genetically engineered cells containing and/or expressing any of the constructs described herein, particularly a construct encoding a protein comprising a composite DNA-binding region, including prokaryotic and eucaryotic cells and in particular, yeast, worm, insect, mouse or other rodent, and other mammalian cells, including any human cells, of various types and lineages, whether frozen or in active growth, whether in culture or in a whole organism containing them. Several examples of such engineered cells are provided in the Examples which follow. Those cells may further contain a DNA sequence to which the encoded chimeric protein is capable of binding. Likewise, this invention encompasses any non-human organism containing such genetically engineered cells. To illustrate this aspect of the invention, an example is provided of a mouse containing engineered cells expressing, in a ligand-dependent manner, an introduced target gene linked to a nucleotide sequence recognized by a chimeric protein containing a composite DNA-binding region.

The foregoing materials and methods permit one to mark a DNA sequence recognized by the chimeric protein as well as to actuate or inhibit the expression of target gene or to cleave the target gene. To do so, one first provides cells containing and capable of expressing a first DNA sequence encoding a chimeric protein which is capable of binding to a second DNA sequence linked to a target gene of interest also present within the cells. The chimeric protein is chosen for its ability to bind to and mark, cleave, actuate or inhibit transcription of, etc. the target gene. The cells are then maintained under conditions permitting gene expression and protein production. Again, gene expression may be inducible or cell-type specific, and the cells may be maintained in culture or within a host organism.

This invention may be applied to virtually any use for which recognition of specific nucleic acid sequences is critical. For instance, the present invention is useful for gene regulation; that is, the novel DNA-binding chimeric proteins can be used for specific activation or repression of transcription of introduced or endogenous genes to control the production of their gene products, whether in cell culture or in whole organisms. In the context of gene therapy, it may be used to correct or compensate for abnormal gene expression, control the expression of disease-causing gene products, direct the expression of a product of a naturally occurring or engineered protein or RNA of therapeutic or prophylactic value, or to otherwise modify the phenotype of cells introduced into or present within an organism, including mammalian subjects, and in particular including human patients. For instance, the invention may be used in gene therapy to increase the expression of a deficient gene product or decrease expression of a product which is overproduced or overactive. This invention may also be used to control gene expression in a transgenic organism for protein production.

The chimeric proteins of the present invention can also be used to identify specific rare DNA sequences, e.g., for use as markers in gene mapping. To identify a DNA sequence in a mixture, one provides a mixture containing one or more DNA sequences; contacts the mixture with a chimeric protein of this invention under conditions permitting the specific binding of a DNA-binding protein to a recognized DNA sequence; and, determines the occurrence, amount and/or location of any DNA binding by the chimeric protein. For example, the chimeric protein may be labeled with a detectable label or with a moiety permitting recovery from the mixture of the chimeric protein with any bound DNA. Using such materials, one may separately recover the chimeric protein and an bound DNA from the mixture and isolate the bound DNA from the protein if desired.

Also, embodiments involving chimeric proteins containing a domain capable of cleaving DNA provide a new series of sequence-specific endonudease proteins. Chimeric DNA-binding proteins of the present invention can also be used to induce or stabilize loop formation in DNA or to bring together or hold together DNA sites on two or more different molecules.

BRIEF DESCRIPTION OF THE DRAWINGS

FIG. 1A–C illustrates selection by ZFHD1 of a hybrid binding site from a pool of random oligonucleotides. FIG. 1A is a graphic representation of the structure of the ZFHD1 chimeric protein used to select binding sites (SEQ ID NO: 75). The underlined residues are from the Zif268-DNA and Oct-1-DNA crystal structures and correspond to the termini used in computer modeling studies. The linker contains two glycines, which were included for flexibility and to help span the required distance between the termini of the domains, and the two arginines that are present at positions −1 and 1 of the Oct-1 homeodomain. A glutathione S-transferase domain (GST) is joined to the amino-terminus of zinc finger 1. FIG. 1B shows the nucleic acid sequences (SEQ ID NOS.: 1–16) of 16 sites isolated after four rounds of binding site selection. These sequences were used to determine the consensus binding sequence (5'-TAATTANGGGNG-3', SEQ ID NO.: 17) of ZFHD1. FIG. 1C shows the alternative possibilities for homeodomain binding configurations suggested by the consensus sequence; Mode 1 was determined to be the correct optimal configuration for ZFHD1. The letter "N" at a position indicates that any nucleotide can occupy is that position.

DETAILED DESCRIPTION OF THE INVENTION

Figure 2A:
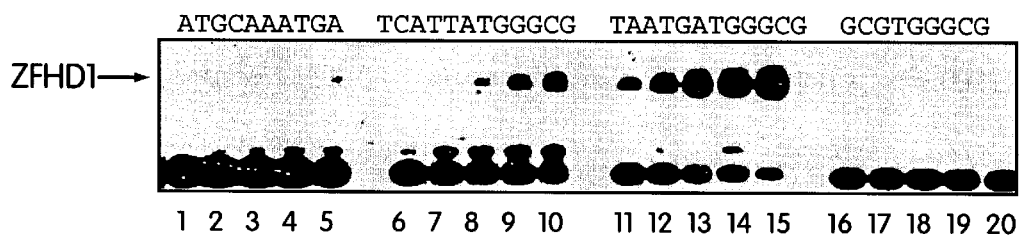
FIG. 2A–C is an autoradiograph illustrating the DNA-binding specificity of ZFHD1, the Oct-1 POU domain and the three zinc fingers from Zif268. The probes used are listed at the top of each set of lanes, and the position of the protein-DNA complex is indicated by the arrow.

This invention pertains to the design, production and use of chimeric proteins containing a composite DNA-binding region, e.g., to obtain constitutive or regulated expression, repression, cleavage or marking of a target gene linked to a nucleotide sequence recognized (i.e., specifically bound) by the chimeric DNA-binding protein. The composite DNA-binding region is a continuous polypeptide chain spanning at least two heterologous polypeptide portions representing component DNA-binding domains. The component polypeptide domains comprise polypeptide sequences derived from at least two different proteins, polypeptide sequences from at least two non-adjacent portions of the same protein, or polypeptide sequences which are not found so linked in nature.

The component polypeptide domains may comprise naturally-occurring or non-naturally occurring peptide sequence. The chimeric protein may include more than two DNA-binding domains. It may also include one or more linker regions comprising one or more amino acid residues, or include no linker, as appropriate, to join the selected domains. The nucleic acid sequence recognized by the chimeric DNA-binding protein may include all or a portion of the sequences bound by the component polypeptide domains. However, the chimeric protein displays a binding specificity that is distinct from the binding specificity of its individual polypeptide components.

The invention further involves DNA sequences encoding such chimeric proteins, the recombinant DNA sequences to which the chimeric proteins bind (i.e., which are recognized by the composite DNA-binding region), constructs containing a target gene and a DNA sequence which is recognized by the chimeric DNA-binding protein, and the use of these materials in applications which depend upon specific recognition of a nucleotide sequence. Such composite proteins and DNA sequences which encode them are recombinant in the sense that they contain at least two constituent portions which are not otherwise found directly linked (covalently) together in nature, at least not in the order, orientation or arrangement present in the recombinant material. Desirable properties of these proteins include high affinity for specific nucleotide sequences, low affinity for most other sequences in a complex genome (such as a mammalian geneome), low dissociation rates from specific DNA sites, and novel DNA recognition specificities distinct from those of known natural DNA-binding proteins. A basic principle of the design is the assembly of multiple DNA-binding domains into a single protein molecule that recognizes a long (sparning at least 10 bases, preferably at least 11 or more bases) and complex DNA sequence with high affinity presumably through the combined interactions of the individual domains. A further benefit of this design is the potential avidity derived from multiple independent protein-DNA interactions. The practice of this invention generally involves expression of a DNA construct encoding and capable of directing the expression in a cell of the chimeric protein containing the composite DNA-binding region and one or more optional, additional domains, as described below. Some embodiments also make use of a DNA construct containing a target gene and one or more copies of a DNA sequence to which the chimeric DNA-binding protein is capable of binding, preferably with high affinity and/or specificity. Some embodiments further involve one or more DNA constructs encoding and directing the expression of additional proteins capable of modulating the activity of the DNA-binding protein, e.g., in the case of chimeras containing ligand-binding domains which complex with one another in the presence of a dimerizing ligand.

In one aspect of the invention, the chimeric proteins are transcription factors which may contain one or more regulatory domains in addition to the composite DNA-binding region. The term "transcription factor" is intended to encompass any protein that regulates gene transcription, and includes regulators that have a positive or a negative effect on transcription initiation or progression. Transcription factors may optionally contain one or more regulatory domains. The term "regulatory domain" is defined as any domain which regulates transcription, and includes both activation domains and repression domains. The term "activation domain" denotes a domain in a transcription factor which positively regulates (turns on or increases) the rate of gene transcription. The term "repression domain" denotes a domain in a transcription factor which negatively regulates (turns off, inhibits or decreases) the rate of gene transcription. The nucleic acid sequence bound by a transcription factor is typically DNA outside the coding region, such as within a promoter or regulatory element region. However, sufficiently tight binding to nucleotides at other locations, e.g., within the coding sequence, can also be used to regulate gene expression.

Preferably the chimeric DNA binding protein binds to a corresponding DNA sequence selectively, i.e., observably binds to that DNA sequence despite the presence of numerous alternative candidate DNA sequences. Preferably, binding of the chimeric DNA-binding protein to the selected DNA sequence is at least two, more preferably three and even more preferably more than four orders of magnitude greater than binding to any one alternative DNA sequence, as may be measured by relative Kd values or by relative rates or levels of transcription of genes associated with the selected and any alternative DNA sequences. It is also preferred that the selected DNA sequence be recognized to a substantially greater degree by the chimeric protein containing the composite DNA-binding region than by a protein containing only some of the individual polypeptide components thereof. Thus, for example, target gene expression is preferably two, more preferably three, and even more preferably more than four orders of magnitude greater in the presence of a chimeric transcription factor containing a composite DNA-binding region than in the presence of a protein containing only some of the components of that composite DNA-binding region.

Additional guidance for practicing various aspects of the invention, together with additional illustrations are provided below.

1. Design of Composite DNA-binding Regions

Each composite DNA-binding region consists of a continuous polypeptide region containing two or more component heterologous polypeptide portions which are individually capable of recognizing (i.e., binding to) specific nucleotide sequences. The individual component portions may be separated by a linker comprising one or more amino acid residues intended to permit the simultaneous contact of each component polypeptide portion with the DNA target. The combined action of the composite DNA-binding region formed by the component DNA-binding modules is thought to result in the addition of the free energy decrement of each set of interactions. The effect is to achieve a DNA-protein interaction of very high affinity, preferably with dissociation constant below $10^{-9}$ M, more preferably below $10^{31\ 10}$ M, even more preferably below $10^{-11}$ M. This goal is often best achieved by combining component polypeptide regions that bind DNA poorly on their own, that is with low affinity, insufficient for functional recognition of DNA under typical conditions in a mammalian cell. Because the hybrid protein exhibits affinity for the composite site several orders of magnitude higher than the affinities of the individual subdomains for their subsites, the protein preferentially (preferably exclusively) occupies the "composite" site which typically comprises a nucleotide sequence spanning the individual DNA sequence recognized by the individual component polypeptide portions of the composite DNA-binding region.

Suitable component DNA-binding polypeptides for incorporation into a composite region have one or more, preferably more, of the following properties. They bind DNA as monomers, although dimers can be accommodated. They should have modest affinities for DNA, with dissociation constants preferably in the range of $10^{-6}$ to $10^{-9}$ M. They should optimally belong to a class of DNA-binding domains whose structure and interaction with DNA are well understood and therefore amenable to manipulation. For gene therapy applications, they are preferably derived from human proteins.

A structure based strategy of fusing known DNA-binding modules has been used to design transcription factors with novel DNA-binding specificities. In order to visualize how certain DNA-binding domains might be fused to other DNA-binding domains, computer modeling studies have been used to superimpose and align various protein-DNA complexes.

Two criteria suggest which alignments of DNA-binding domains have potential for combination into a composite DNA-binding region (1) lack of collision between domains, and (2) consistent positioning of the carboxyl- and amino-terminal regions of the domains, ie., the domains must be oriented such that the carboxyl-terminal region of one polypeptide can be joined to the amino-terminal region of the next polypeptide, either directly or by a linker (indirectly). Domains positioned such that only the two amino-terminal regions are adjacent to each other or only the two carboxyl-terminal regions are adjacent to each other are not suitable for inclusion in the chimeric proteins of the present invention. When detailed structural information about the protein-DNA complexes is not available, it may be necessary to experiment with various endpoints, and more biochemical work may be necessary to characterize the DNA-binding properties of the chimeric protein. This optimization can be performed using known techniques. Virtually any domains satisfying the above-described criteria are candidates for inclusion in the chimeric protein. Alternatively, non-computer modeling may also be used.

2. Examples of Suitable Component DNA-binding Domains

DNA-binding domains with appropriate DNA binding properties may be selected from several different types of natural DNA-binding proteins. One class comprises proteins that normally bind DNA only in conjunction with auxiliary DNA-binding proteins, usually in a cooperative fashion, where both proteins contact DNA and each protein contacts the other. Examples of this class include the homeodomain proteins, many of which bind DNA with low affinity and poor specificity, but act with high levels of specificity in vivo due to interactions with partner DNA-binding proteins. One well-characterized example is the yeast alpha2 protein, which binds DNA only in cooperation with another yeast protein Mcm1. Another example is the human homeodomain protein Phox1, which interacts cooperatively with the human transcription factor, serum response factor (SRF).

The homeodomain is a highly conserved DNA-binding domain which has been found in hundreds of transcription factors (Scott et al., *Biochim. Biophys. Acta* 9:25–48 (1989) and Rosenfeld, *Genes Dev.* 5:897–907 (1991)). The regulatory function of a homeodomain protein derives from the specificity of its interactions with DNA and presumably with components of the basic transcriptional machinery, such as RNA polymerase or accessory transcription factors (Laughon, *Biochemistry* 30(48):11357 (1991)). A typical homeodomain comprises an approximately 61-amino acid residue polypeptide chain, folded into three alhpha helices which binds to DNA.

A second class comprises proteins in which the DNA-binding domain is comprised of multiple reiterated modules that cooperate to achieve high-affinity binding of DNA. An example is the C2H2 class of zinc-finger proteins, which typically contain a tandem array of from two or three to dozens of zinc-finger modules. Each module contains an alpha-helix capable of contacting a three base-pair stretch of DNA. Typically, at least three zinc-fingers are required for high-affinity DNA binding. Therefore, one or two zinc-fingers constitute a low-affinity DNA-binding domain with suitable properties for use as a component in this invention. Examples of proteins of the C2H2 class include TFIIIA, Zif268, Gli, and SRE-ZBP. (These and other proteins and DNA sequences referred to herein are well known in the art. Their sources and sequences are known.)

The zinc finger motif, of the type first discovered in transcription factor IIIA (Miller et al., *EMBO J.* 4:1609 (1985)), offers an attractive framework for studies of transcription factors with novel DNA-binding specificities. The zinc finger is one of the most common eukaryotic DNA-binding motifs (Jacobs, *EMBO J.* 11:4507 (1992)), and this family of proteins can recognize a diverse set of DNA sequences (Pavletich and Pabo, *Science* 261:1701 (1993)). Crystallographic studies of the Zif268-DNA complex and other zinc finger-DNA complexes show that residues at four positions within each finger make most of the base contacts, and there has been some discussion about rules that may explain zinc finger-DNA recognition (Desjarlais and Berg, *PNAS* 89:7345 (1992) and Klevit, *Science* 253:1367 (1991)). However, studies have also shown that zinc fingers can dock against DNA in a variety of ways (Pavletich and Pabo (1993) and Fairall et al., *Nature* 366:483 (1993)).

A third general class comprises proteins that themselves contain multiple independent DNA-binding domains. Often, any one of these domains is insufficient to mediate high-affinity DNA recognition, and cooperation with a covalently linked partner domain is required. Examples include the POU class, such as Oct-1, Oct-2 and Pit-1, which contain both a homeodomain and a POU-specific domain; HNF1, which is organized similarly to the POU proteins; certain Pax proteins (examples: Pax-3, Pax-6), which contain both a homeodomain and a paired box/domain; and XXX, which contains a homeodomain and multiple zinc-fingers of the C2H2 class.

From a structural perspective, DNA-binding proteins containing domains suitable for use as polypeptide components of a composite DNA-binding region may be classified as DNA-binding proteins with a helix-turn-helix structural design, including, but not limited to, MAT α1, MAT α2, MAT a1, Antennapedia, Ultrabithorax, Engrailed, Paired, Fushi tarazu, HOX, Unc86, and the previously noted Oct1, Oct2 and Pit; zinc finger proteins, such as Zif268, SWI5, Krüppel and Hunchback; steroid receptors; DNA-binding proteins with the helix-loop-helix structural design, such as Daughterless, Achaete-scute T3), MyoD, E12 and E47; and other helical motifs like the leucine-zipper, which includes GCN4, C/EBP, c-Fos/c-Jun and JunB. The amino acid sequences of the component DNA-binding domains may be naturally occurring or non-naturally-occurring occurring (or modified).

The choice of component DNA-binding domains may be influenced by a number of considerations, including the species, system and cell type which is targeted; the feasibility of incorporation into a chimeric protein, as may be shown by modeling; and the desired application or utility. The choice of DNA-binding domains may also be influenced by the individual DNA sequence specificity of the domain and the ability of the domain to interact with other proteins or to be influenced by a particular cellular regulatory pathway. Preferably, the distance between domain termini is relatively short to facilitate use of the shortest possible linker or no linker. The DNA-binding domains can be isolated from a naturally-occurring protein, or may be a synthetic molecule based in whole or in part on a naturally-occurring domain.

An additional strategy for obtaining component DNA-binding domains with properties suitable for this invention is to modify an existing DNA-binding domain to reduce its affinity for DNA into the appropriate range. For example, a homeodomain such as that derived from the human transcription factor Phox1, may be modified by substitution of the glutamine residue at position 50 of the homeodomain. Substitutions at this position remove or change an important point of contact between the protein and one or two base pairs of the 6-bp DNA sequence recognized by the protein. Thus, such substitutions reduce the free energy of binding and the affinity of the interaction with this sequence and may or may not simultaneously increase the affinity for other sequences. Such a reduction in affinity is sufficient to effectively eliminate occupancy of the natural target site by this protein when produced at typical levels in mammalian cells. But it would allow this domain to contribute binding energy to and therefore cooperate with a second linked DNA-binding domain. Other domains that amenable to this type of manipulation include the paired box, the zinc-finger class represented by steroid hormone receptors, the myb domain, and the ets domain.

3. Design of Linker Sequence for Covalently Linked Composite DBDs

The continuous polypeptide span of the composite DNA-binding domain may contain the component polypeptide modules linked directly end-to-end or linked indirectly via an intervening amino acid or peptide linker. A linker moiety may be designed or selected empirically to permit the independent interaction of each component DNA-binding domain with DNA without steric interference. A linker may also be selected or designed so as to impose specific spacing and orientation on the DNA-binding domains. The linker amino adds may be derived from endogenous flanking peptide sequence of the component domains or may comprise one or more heterologous amino acids. Linkers may be designed by modeling or identified by experimental trial.

The linker may be any amino acid sequence that results in linkage of the component domains such that they retain the ability to bind their respective nucleotide sequences. In some embodiments it is preferable that the design involve an arrangement of domains which requires the linker to span a relatively short distance, preferably less than about 10 Å. However, in certain embodiments, depending upon the selected DNA-binding domains and the configuration, the linker may span a distance of up to about 50 Å. For instance, the ZFHD1 protein contains a glycine-glycine-arginine-arginine linker which joins the carboxyl-terminal region of zinc finger 2 to the amino-terminal region of the Oct-1 homeodomain.

Within the linker, the amino acid sequence may be varied based on the preferred characteristics of the linker as determined empirically or as revealed by modeling. For instance, in addition to a desired length, modeling studies may show that side groups of certain nucleotides or amino acids may interfere with binding of the protein. The primary criterion is that the linker join the DNA-binding domains in such a manner that they retain their ability to bind their respective DNA sequences, and thus a linker which interferes with this ability is undesirable. A desirable linker should also be able to constrain the relative three-dimensional positioning of the domains so that only certain composite sites are recognized by the chimeric protein. Other considerations in choosing the linker include flexibility of the linker, charge of the linker and selected binding domains, and presence of some amino acids of the linker in the naturally-occurring domains. The linker can also be designed such that residues in the linker contact DNA, thereby influencing binding affinity or specificity, or to interact with other proteins. For example, a linker may contain an amino acid sequence which can be recognized by a protease so that the activity of the chimeric protein could be regulated by deavage. In some cases, particularly when it is necessary to span a longer distance between the two DNA-binding domains or when the domains must be held in a particular configuration, the linker may optionally contain an additional folded domain.

Additional Domains

Additional domains may be included in the various chimeric proteins of this invention, e.g. A nuclear localization sequence, a transcription regulatory domain, a ligand binding domain, a protein-binding domain, a domain capable of cleaving a nucleic acid, etc.

For example, in some embodiments the chimeric proteins will contain a cellular targeting sequence which provides for the protein to be translocated to the nucleus. Typically a nuclear localization sequence has a plurality of basic amino acids, referred to as a bipartite basic repeat (reviewed in Garcia-Bustos et al, Biochimica et Biophysica Acta (1991) 1071, 83–101). This sequence can appear in any portion of the molecule internal or proximal to the N- or C-terminus and results in the chimeric protein being localized inside the nucleus.

The chimeric proteins may include domains that facilitate their purification, e.g. "histidine tags" or a glutathionetransferase domain. They may include "epitope tags" encoding peptides recognized by known monoclonal antibodies for the detection of proteins within cells or the capture of proteins by antibodies in vitro A chimeric DNA-binding protein which contains a domain with endonuclease activity (a cleavage domain) can also be used as a novel sequence-specific restriction endonucleases to cleave DNA adjacent to the recognition sequence bound by the chimeric protein. For example, such a chimeric protein may containing a composite DNA-binding region and the C-terminal cleavage domain of Fok I endonuclease, which has nonspecific DNA-cleavage activity (Li et al., *Proc. Natl. Acad. Sci. USA* 89:4275–4279 (1992)).

Site-specific restriction enzymes can also be linked to other DNA-binding domains to generate endonucleases with very strict sequence requirements. The chimeric DNA-binding proteins can also be fused to other domains that can control the stability, association and subcellular ocalization of the new proteins.

The chimeric protein may also include one or more transcriptional activation domains, such as the well characterized domain from the viral protein VP16 or novel activation domains of different designs. For instance, one may use one or multiple copies of transcriptional activating motifs from human proteins, including e.g. the 18 amino acid (NFLQLPQQTQGALLTSQP) (SEQ ID NO: 31) glutamine rich region of Oct-2, the N-terminal 72 amino acids of p53, the SYGQQS repeat in Ewing sarcoma gene or an 11 amino acid (535–545) acidic rich region of Rel A protein. Chimeric proteins which contain both a composite DNA-binding domain and a transcriptional activating domain thus comprise composite transcription factors capable of actuating transcription of a target gene linked to a DNA sequence recognized by the chimeric protein. The chimeric proteins may include regulatory domains that place the function of the DNA-binding domain under the control of an external ligand; one example would be the ligand-binding domain of steroid receptors.

The chimeric proteins may also include a ligand-binding domain to provide for regulatable interaction of the protein with a second polypeptide chain. In such cases, the presence of a ligand-binding domain permits association of the chimeric DNA-binding protein, in the presence of a dimerizing ligand, with a second chimeric protein containing a transcriptional regulatory domain (activator or repressor) and another ligandbinding domain. Upon dimerization of the chimeras a composite DNA-binding protein complex is formed which further contains the transcriptional regulatory domain and any other optional domains.

Multimerizing ligands useful in practicing this invention are multivalent, i.e., capable of binding to, and thus multimerizing, two or more of the chimeric protein molecules. The multimerizing ligand may bind to the chimeras containing such ligand-binding domains, in either order or simultaneously, preferably with a Kd value below about $10^{-6}$, more preferably below about $10^{-7}$, even more preferably below about $10^{-8}$, and in some embodiments below about $10^{-9}$ M. The ligand preferably is not a protein or polypeptide and has a molecular weight of less than about 5 kDa, preferably below 2 kDa. The ligand-binding domains of the chimeric proteins so multimerized may be the same or different. Ligand binding domains include among others, various immunophilin domains. One example is the FKBP domain which is capable of binding to dimerizing ligands incorporating FK506 moieties or other FKBP-binding moieties. See e.g. PCT/US93/01617, the full contents of which are hereby incorporated by reference.

Illustrating the class of chimeric proteins of this invention which contain a composite DNA-binding domain comprising at least one homeodomain and at least one zinc finger domain are a set of chimeric proteins in which the composite DNA-binding region comprises an Oct-1 homeodomain and zinc fingers 1 and 2 of Zif268, referred to herein as "ZFHD1". Proteins comprising the ZFHD1 composite DNA-binding region have been produced and shown to bind a composite DNA sequence (SEQ ID NO.: 17) which includes the nucleic acid sequences bound by the relevant portion of the two component DNA-binding proteins.

Illustrating the class of chimeric DNA-binding proteins of this invention which further contain at least one transcription activation domain are chimeric proteins containing the ZFHD1 composite DNA-binding region and the Herpes Simplex Virus VP16 activation domain, which has been produced and shown to activate transcription selectively in vivo of a gene (the luciferase gene) linked to an iterated ZFHD1 binding site. Another chimeric protein containing ZFHD1 and a NF-κB p65 activation domain has also been produced and shown to activate transcription in vivo of a gene (secreted alkaline phosphatase) linked to iterated ZFHD1 binding sites.

Transcription factors can be tested for activity in vivo using a simple assay (F. M. Ausubel et al., Eds., CURRENT PROTOCOLS IN MOLECULAR BIOLOGY (John Wiley & Sons, New York, 1994); de Wet et al., *Mol. Cell Biol.* 7:725 (1987)). The in vivo assay requires a plasmid containing and capable of directing the expression of a recombinant DNA sequence encoding the transcription factor. The assay also requires a plasmia containing a reporter gene, e.g., the luciferase gene, the chloramphenicol acetyl transferase (CAT) gene, secreted alkaline phosphatase or the human growth hormone (hGH) gene, linked to a binding site for the transcription factor. The two plasmids are introduced into host cells which normally do not produce interfering levels of the reporter gene product. A second group of cells, which also lack both the gene encoding the transcription factor and the reporter gene, serves as the control group and receives a plasmid containing the gene encoding the transcription factor and a plasmid containing the test gene without the binding site for the transcription factor.

The production of mRNA or protein encoded by the reporter gene is measured. An increase in reporter gene expression not seen in the controls indicates that the transcription factor is a positive regulator of transcription. If reporter gene expression is less than that of the control, the transcription factor is a negative regulator of transcription.

Optionally, the assay may include a transfection efficiency control plasmid. This plasmid expresses a gene product independent of the test gene, and the amount of this gene product indicates roughly how many cells are taking up the plasmids and how efficiently the DNA is being introduced into the cells. Additional guidance on evaluating chimeric proteins of this invention is provided below.

Design and Assembly of Constructs

DNA sequences encoding individual DNA-binding subdomains and linkers, if any, are joined such that they constitute a single open reading frame encoding a chimeric protein containing the composite DNA-binding region and capable of being translated in cells or cell lysates into a single polypeptide harboring all component domains. This protein-encoding DNA sequence is then placed into a conventional plasmid vector that directs the expression of the protein in the appropriate cell type. For testing of proteins and determination of binding specificity and affinity, it may be desirable to construct plasmids that direct the expression of the protein in bacteria or in reticulocyte-lysate systems. For use in the production of proteins in mammalian cells, the protein-encoding sequence is introduced into an expression vector that directs expression in these cells. Expression vectors suitable for such uses are well known in the art. Various sorts of such vectors are commercially available.

In embodiments involving composite DNA-binding proteins or accessory chimeric proteins which contain multiple domains, e.g. proteins containing a ligand binding domain and/or a transcription regulatory domain, DNA sequences encoding the constituent domains, with any introduced sequence alterations may be ligated or otherwise joined together such that they constitute a single open reading frame that can be translated in cells into a single polypeptide harboring all constituent domains. The order and arrangement of the domains within the polypeptide can vary as desired.

6. Target DNA Sequence

The DNA sequences recognized by a chimeric protein containing a composite DNA-binding domain can be determined experimentally, as described below, or the proteins can be manipulated to direct their specificity toward a desired sequence. A desirable nucleic acid recognition sequence consists of a nucleotide sequence spanning at least ten, preferably eleven, and more preferably twelve or more bases. The component binding portions (putative or demonstrated) within the nucleotide sequence need not be fully contiguous; they may be interspersed with "spacer" base pairs that need not be directly contacted by the chimeric protein but rather impose proper spacing between the nucleic acid subsites recognized by each module. These sequences should not impart expression to linked genes when introduced into cells in the absence of the engineered DNA-binding protein.

To identify a nucleotide sequence that is recognized by a chimeric protein containing the composite DNA-binding region, preferably recognized with high affinity (dissociation constant $10^{-11}$ M or lower are especially preferred), several methods can be used. If high-affinity binding sites for individual subdomains of the composite DNA-binding region are already known, then these sequences can be joined with various spacing and orientation and the optimum configuration determined experimentally (see below for methods for determining affinities). Alternatively, high-affinity binding sites for the protein or protein complex can be selected from a large pool of random DNA sequences by adaptation of published methods (Pollock, R and Treisman, R., 1990, A sensitive method for the determination of protein-DNA binding specificities. *Nucl. Acids Res.* 18, 6197–6204). Bound sequences are cloned into a plasmid and their precise sequence and affinity for the proteins are determined. From this collection of sequences, individual sequences with desirable characteristics (i.e., maximal affinity for composite protein, minimal affinity for individual subdomains) are selected for use. Alternatively, the collection of sequences is used to derive a consensus sequence that carries the favored base pairs at each position. Such a consensus sequence is synthesized and tested (see below) to confirm that it has an appropriate level of affinity and specificity.

7. Design of Target Gene Construct

A DNA construct that enables the target gene to be regulated, cleaved, etc. by DNA-binding proteins of this invention is a fragment, plasmid, or other nucleic acid vector carrying a synthetic transcription unit typically consisting of: (1) one copy or multiple copies of a DNA sequence recognized with high-affinity by the composite DNA-binding protein; (2) a promoter sequence consisting minimally of a TATA box and initiator sequence but optionally including other transcription factor binding sites; (3) sequence encoding the desired product (protein or RNA), including sequences that promote the initiation and termination of translation, if appropriate; (4) an optional sequence consisting of a splice donor, splice acceptor, and intervening intron DNA; and (5) a sequence directing cleavage and polyadenylation of the resulting RNA transcript.

8. Determination of Binding Affinity

A number of well-characterized assays are available for determining the binding affinity, usually expressed as dissociation constant, for DNA-binding proteins and the cognate DNA sequences to which they bind. These assays usually require the preparation of purified protein and binding site (usually a synthetic oligonucleotide) of known concentration and specific activity. Examples include electrophoretic mobility-shift assays, DNaseI protection or "footprinting", and filter-binding. These assays can also be used to get rough estimates of association and dissociation rate constants. These values may be determined with greater precision using a BIAcore instrument, In this assay, the synthetic oligonucleotide is bound to the assay "chip," and purified DNA-binding protein is passed through the flow-cell. Binding of the protein to the DNA immobilized on the chip is measured as an increase in refractive index. Once protein is bound at equilibrium, buffer without protein is passed over the chip, and the dissociation of the protein results in a return of the refractive index to baseline value. The rates of association and dissociation are calculated from these curves, and the affinity or dissociation constant is calculated from these rates. Binding rates and affinities for the high affinity composite site may be compared with the values obtained for subsites recognized by each subdomain of the protein. As noted above, the difference in these dissociation constants should be at least two orders of magnitude and preferably three or greater.

9. Testing for Function in vivo

Several tests of increasing stringency may be used to confirm the satisfactory performance of a DNA-binding protein designed according to this invention. AU share essentially the same components: (1) (a) an expression plasmid directing the production of a chimeric protein comprising the composite DNA-binding region and a potent transcriptional activation domain or (b) one or more expression plasmids directing the production of a pair of chimeric proteins of this invention which are capable of dimerizing in the presence of a corresponding dimerizing agent, and thus forming a protein complex containing a composite DNA-binding region on one protein and a transcription activation domain on the other; and (2) a reporter plasmid directing the expression of a reporter gene, preferably identical in design to the target gene described above (i.e., multiple binding sites for the DNA-binding domain, a minimal promoter element, and a gene body) but encoding any conveniently measured protein.

In a transient transfection assay, the above-mentioned plasmids are introduced together into tissue culture cells by any conventional transfection procedure, including for example calcium phosphate coprecipitation, electroporation, and lipofection. After an appropriate time period, usually 24–48 hr, the cells are harvested and assayed for production of the reporter protein. In embodiments requiring dimerization of chimeric proteins for activation of transcription, the assay is conducted in the presence of the dimerizing agent In an appropriately designed system, the reporter gene should exhibit little activity above background in the absence of any co-transfected plasmid for the composite transcription factor (or in the absence of dimerizing agent in embodiments under dimerizer control). In contrast, reporter gene expression should be elevated in a dose-dependent fashion by the inclusion of the plasmid encoding the composite transcription factor (or plasmids encoding the multimerizable chimeras, following addition of multimerizing agent). This result indicates that there are few natural transcription factors in the recipient cell with the potential to recognize the tested binding site and activate transcription and that the engineered DNA-binding domain is capable of binding to this site inside living cells.

The transient transfection assay is not an extremely stringent test in most cases, because the high concentrations of plasmid DNA in the transfected cells lead to unusually high concentrations of the DNA-binding protein and its recognition site, allowing functional recognition even with relative low affinity interactions. A more stringent test of the system is a transfection that results in the integration of the introduced DNAs at near single-copy. Thus, both the protein concentration and the ratio of specific to non-specific DNA sites would be very low; only very high affinity interactions would be expected to be productive. This scenario is most readily achieved by stable transfection in which the plasmids are transfected together with another DNA encoding an unrelated selectable marker (e.g., G418-resistance). Transfected cell clones selected for drug resistance typically contain copy numbers of the nonselected plasmids ranging from zero to a few dozen. A set of clones covering that range of copy numbers can be used to obtain a reasonably clear estimate of the efficiency of the system.

Perhaps the most stringent test involves the use of a viral vector, typically a retrovirus, that incorporates both the reporter gene and the gene encoding the composite transcription factor or multimerizable components thereof. Virus stocks derived from such a construction will generally lead to single-copy transduction of the genes.

If the ultimate application is gene therapy, it may be preferred to construct transgenic animals carrying similar DNAs to determine whether the protein is functional in an animal.

11. Introduction of Constructs into Cells

Constructs encoding the chimeras containing a composite DNA-binding region, constructs encoding related chimeric proteins (e.g. in the case of ligand-dependent a petitions) and constructs directing the expression of target genes, all as described herein, can be introduced into cells as one or more DNA molecules or constructs, in many cases in association with one or more markers to allow for selection of host cells which contain the construct(s). The constructs can be prepared in conventional ways, where the coding sequences and regulatory regions may be isolated, as appropriate, ligated, cloned in an appropriate cloning host, analyzed by restriction or sequencing, or other convenient means. Particularly, using PCR, individual fragments including all or portions of a functional unit may be isolated, where one or more mutations may be introduced using "primer repair", ligation, in vitro mutagenesis, etc. as appropriate. The construct(s) once completed and demonstrated to have the appropriate sequences may then be introduced into a host cell by any convenient means. The constructs may be integrated and packaged into non-replicating, defective viral genomes like Adenovirus, Adeno-associated virus (AAV), or Herpes simplex virus (HSV) or others, including retroviral vectors, for infection or transduction into cells. The constructs may include viral sequences for transfection, if desired. Alternatively, the construct may be introduced by fusion, electroporation, biolistics, transfection, lipofection, or the like. The host cells will in some cases be grown and expanded in culture before introduction of the construct(s), followed by the appropriate treatment for introduction of the construct(s) and integration of the construct(s). The cells will then be expanded and screened by virtue of a marker present in the construct. Various markers which may be used successfully include hprt, neomycin resistance, thyrnidine kinase, hygromycin resistance, etc.

In some instances, one may have a target site for homologous recombination, where it is desired that a construct be integrated at a particular locus. For example, one can delete and/or replace an endogenous gene (at the same locus or elsewhere) with a recombinant target construct of this invention. For homologous recombination, one may generally use either Ω or O-vectors. See, for example, Thomas and Capecchi, *Cell (*1987) 51, 503–512; Mansour, et al., *Nature* (1988) 336, 348–352; and Joyner, et al., *Nature* (1989) 338, 153–156.

The constructs may be introduced as a single DNA molecule encoding all of the genes, or different DNA molecules having one or more genes. The constructs may be introduced simultaneously or consecutively, each with the same or different markers.

Vectors containing useful elements such as bacterial or yeast origins of replication, selectable and/or amplifiable markers, promoter/enhancer elements for expression in procaryotes or eucaryotes, etc. which may be used to prepare stocks of construct DNAs and for carrying out transfections are well known in the art, and many are commercially available.

Introduction of Constructs into Animals

Cells which have been modified ex vivo with the DNA constructs may be grown in culture under selective conditions and cells which are selected as having the desired construct(s) may then be expanded and further analyzed, using, for example, the polymerase chain reaction for determining the presence of the construct in the host cells. Once modified host cells have been identified, they may then be used as planned, e.g. grown in culture or introduced into a host organism.

Depending upon the nature of the cells, the cells may be introduced into a host organism, e.g. a mammal, in a wide variety of ways. Hematopoietic cells may be administered by injection into the vascular system, there being usually at least about $10^4$ cells and generally not more than about $10^{10}$, more usually not more than about $10^8$ cells. The number of cells which are employed will depend upon a number of circumstances, the purpose for the introduction, the lifetime of the cells, the protocol to be used, for example, the number of administrations, the ability of the cells to multiply, the stability of the therapeutic agent, the physiologic need for the therapeutic agent, and the like. Alternatively, with skin cells which may be used as a graft, the number of cells would depend upon the size of the layer to be applied to the bum or other lesion. Generally, for myoblasts or fibroblasts, the number of cells will be at least about $10^4$ and not more than about 108 and may be applied as a dispersion, generally being injected at or near the site of interest. The cells will usually be in a physiologically-acceptable medium.

Cells engineered in accordance with this invention may also be encapsulated, e.g. using conventional materials and methods. See e.g. Uludag and Sefton, 1993, *J Biomed. Mater. Res.* 27(10):1213–24; Chang et al, 1993, *Hum Gene Ther* 4(4):433–40; Reddy et al, 1993, *J Infect Dis* 168(4):1082–3; Tai and Sun, 1993, *FASEB J* 7(11):1061–9; Emerich et al, 1993, Exp Neurol 122(1)37:–47; Sagen et al, 1993, *Neurosci* 13(6):2415–23; Aebischer et al, 1994, *Exp Neurol* 126(2) 151–8; Savelkoul et al, 1994, *J Immunol Methods* 170(2):185–96; Winn et al, 1994, *PNAS USA* 91 (6):2324–8; Emerich et al, 1994, *Prog Neuropsychopharmacol Biol Psychiatry* 18(5):935–46 and Kordower et al, 1994, *PNAS USA* 91(23):10898–902. The cells may then be introduced in encapsulated form into an animal host, preferably a mammal and more preferably a human subject in need thereof. Preferably the encapsulating material is semipermeable, permitting release into the host of secreted proteins produced by the encapsulated cells. In many embodiments the semipermeable encapsulation renders the encapsulated cells immunologically isolated from the host organism in which the encapsulated cells are introduced. In those embodiments the cells to be encapsulated may express one or more chimeric proteins containing components domains derived from viral proteins or proteins from other species.

Instead of ex vivo modification of the cells, in many situations one may wish to modify cells in vivo. For this purpose, various techniques have been developed for modification of target tissue and cells in vivo. A number of virus vectors have been developed, such as adenovirus, adeno-associated virus. and retroviruses, which allow for transfection and random integration of the virus into the host. See, for example, Debunks et al. (1984) *Proc. Natl. Acad. Sci. USA* 81, 7529–7533; Caned et al., (1989) *Science* 243, 375–378; Hiebert et al. (1989) *Proc. Natl. Acad. Sci. USA* 86, 3594–3598; Hatzoglu et al. (1990) *J. Biol. Chem.* 265, 17285–17293 and Ferry, et al. (1991) *Proc. Natl. Acad. Sci. USA* 88, 8377–8381. The vector may be administered by injection, e.g. intravascularly or intramuscularly, inhalation, or other parenteral mode.

In accordance with in vivo genetic modification, the manner of the modification will depend on the nature of the tissue, the efficiency of cellular modification required, the number of opportunities to modify the particular cells, the accessibility of the tissue to the DNA composition to be introduced, and the like. By employing an attenuated or modified retrovirus carrying a target transcriptional initiation region, if desired, one can activate the virus using one of the subject transcription factor constructs, so that the virus may be produced and transfect adjacent cells.

The DNA introduction need not result in integration in every case. In some situations, transient maintenance of the DNA introduced may be sufficient In this way, one could have a short term effect, where cells could be introduced into the host and then turned on after a predetermined time, for example, after the cells have been able to home to a particular site.

13. ZFHD1

Illustrating one design approach, Example 1 describes computer modeling studies which were used to determine the orientation and linkage of potentially useful DNA-binding domains (see Example 1). Computer modeling studies allowed manipulation and superimposition of the crystal structures of Zif268 and Oct-1 protein-DNA complexes. This study yielded two arrangements of the domains which appeared to be suitable for use in a chimeric protein. In one alignment, the carboxyl-terminal region of zinc finger 2 was 8.8 Å away from the amino-terminal region of the homeodomain, suggesting that a short polypeptide could connect these domains. In this model, the chimeric protein would bind a hybrid DNA site with the sequence 5'-AAATNNTGGGCG-3' (SEQ ID NO.: 18). The Oct-1 homeodomain would recognize the AAAT subsite, zinc finger 2 would recognize the TGG subsite, and zinc finger 1 would recognize the GCG subsite. No risk of steric interference between the domains was apparent in this model. This arrangement was used in the work described below and in the Examples.

The second plausible arrangement would also have a short polypeptide linker spanning the distance from zinc finger 2 to the homeodomain (less than 10 Å); however, the subsites are arranged so that the predicted binding sequence is 5'-CGCCCANNAAAT-3' (SEQ ID NO.: 19). This arrangement was not explicitly used in the work described below, although the flexibility of the linker region may also allow ZFHD1 to recognize this site.

After selecting a suitable arrangement, construction of the corresponding molecule was carried out. Generally, sequences may be added to the chimeric protein to facilitate expression, detection, purification or assays of the product by standard methods. A glutathione S-transferase domain (GST) was attached to ZFHD1 for these purpose (see Example 2).

The consensus binding sequence of the chimeric protein ZFHD1 was determined by selective binding studies from a random pool of oligonucleotides. The oligonucleotide sequences bound by the chimeric protein were sequenced and compared to determine the consensus binding sequence for the chimeric protein (see Example 3 and FIG. 1).

After four rounds of selection, 16 sites were cloned and sequenced (SEQ ID NOS.: 1–16, FIG. 1B). Comparing these sequences revealed the consensus binding site 5'-TAATTANGGGNG-3'(SEQ ID NO.: 17). The 5' half of this consensus, TAATTA, resembled a canonical homeodomain binding site TAATNN (Laughon, (1991)), and matched the site (TAATNA) that is preferred by the Oct-1 homeodomain in the absence of the POU-specific domain (Verrijzer et al., *EMBO J*. 11:4993 (1992)). The 3' half of the consensus, NGGGNG, was consistent with adjacent binding sites for fingers 2 (TGG) and 1 (GCG) of Zif268.

Binding studies were performed in order to determine the ability of the chimeric protein ZFHD1 to distinguish the consensus sequence from the sequences recognized by the component polypeptides of the composite DNA-binding region. ZFHD1, the Oct-1POU domain (containing a homeodomain and a POU-specific domain), and the three zinc fingers of Zif268 were compared for their abilities to distinguish among the Oct1 site 5'-ATGCAAATGA-3' (SEQ ID NO.: 20), the Zif268 site 5'-GCGTGGGCG-3' and the hybrid binding site 5'-TAATGATGGGCG-3' (SEQ ID NO.: 21). The chimeric protein ZFHD1 preferred the optimal hybrid site to the octamer site by a factor of 240 and did not bind to the Zif site. The POU domain of Oct1 bound to the octamer site with a dissociation constant of $1.8 \times 10^{-10}$ M under the assay conditions used, preferring this site to the hybrid sequences by factors of 10 and 30, and did not bind to the Zif site. The three zinc fingers of Zif268 bound to the Zif site with a dissociation constant of $3.3 \times 10^{-10}$M, and did not bind to the other three sites. These experiments show that ZFHD1 binds tightly and specifically to the hybrid site and displayed DNA-binding specificity that was clearly distinct from that of either of the original proteins.

Figure 3:
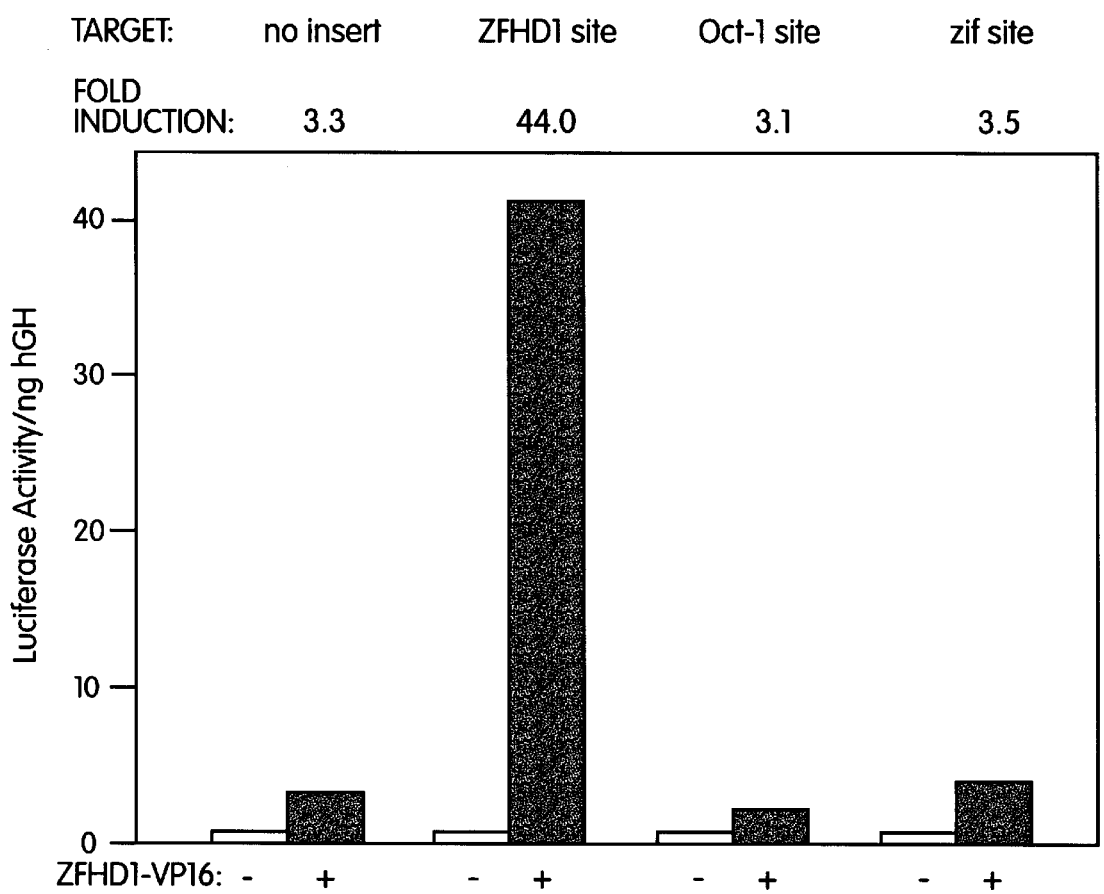
FIG. 3 is a graphic representation of the regulation of promoter activity in vivo by ZFHD1. The expression vector encoded the ZFHD1 protein fused to the carboxyl-terminal 81 amino acids of VP16 (+bars), and the empty expression vector Rc/CMV was used as control (−bars). Bar graphs represent the average of three independent trials. Actual values and standard deviation reading from left to right are: 1.00±0.05, 330±0.63; 0.96±0.08, 42.2±5.1; 0.76±07, 2.36±0.34; 1.22±0.10, 4.22±1.41. Fold induction refers to the level of normalized activity obtained with the ZFHD1-VP16 expression construct divided by that obtained with Rc/CMV.

In order to determine whether the novel DNA-binding protein could function in vivo, ZFHD1 was fused to a transcriptional activation domain to generate a transcription factor, and transfection experiments were performed (see Example 5). An expression plasmid encoding ZFHD1 fused to the carboxyl-terminal 81 amino acids of the Herpes Simplex Virus VP16 protein (ZFHD1-VP16) was co-transfected into 293 cells with reporter constructs containing the SV40 promoter and the firefly luciferase gene (FIG. 3). To determine whether the chimeric protein could specifically regulate gene expression, reporter constructs containing two tandem copies of either the ZfHD1 site 5'-TAATGATGGGCG-3' (SEQ ID NO.: 21), the octamer site 5'-ATGCAAATGA-3' (SEQ ID NO.: 20) or the Zif site 5'-CGTGGGCG-3' inserted upstream of the SV40 promoter were tested. When the reporter contained two copies of the ZFHD1 site, the ZFHD1-VP16 protein stimulated the activity of the promoter in a dose-dependent manner. Furthermore, the stimulatory activity was specific for the promoter containing the ZFHD1 binding sites. At levels of protein which stimulated this promoter by 44-fold, no stimulation above background was observed for promoters containing the octamer or Zif sites. Thus, ZFHD1 efficiently and specifically recognized its target site in vivo.

Utilizing the above-described procedures and known DNA-binding domains, other novel chimeric transcription factor proteins can be constructed. These chimeric proteins can be studied as disclosed herein to determine the consensus binding sequence of the chimeric protein. The binding specificity, as well as the in vivo activity, of the chimeric protein can also be determined using the procedures illustrated herein. Thus, the methods of this invention can be utilized to create various chimeric proteins from the domains of DNA-binding proteins.

14. Optimization and Engineering of Composite DNA-binding Regions

The useful range of composite DNA binding regions is not limited to the specifities that can be obtained by linking two naturally occurring DNA binding subdomains. A variety of mutagenesis methods can be used to alter the binding specificity. These include use of the crystal or NMR structures (3D) of complexes of a DNA-binding domain (DBD) with DNA to rationally predict (an) amino acid substitution (s) that will alter the nucleotide sequence specificity of DNA binding, in combination with computational modelling approaches. Candidate mutants can then be engineered and expressed and their DNA binding specificity identified using oligonucleotide site selection and DNA sequencing, as described earlier.

An alternative approach to generating novel sequence specificities is to use databases of known homologs of the DBD to predict amino acid substitutions that will alter binding. For example, analysis of databases of zinc finger sequences has been used to alter the binding specificity of a zinc finger (Desjarlais and Berg (1993) Proc. Natl. Acad. Sci. USA 90, 2256–2260).

A further and powerful approach is random mutaganesis of amino acid residues which may contact the DNA, followed by screening or selection for the desired novel specificity. Preferably, the libraries are surveyed using phage display so that mutants can be directly selected. For example, phage display of the three fingers of Zi 268 (including the two incorporated into ZFHD1) has been described, and random mutagenesis and selection has been used to alter the specificity and affinity of the fingers (Rebar and Pabo (1994) Science 263, 671– 673; Jamieson et al, (1994) Biochemistry 33, 5689–5695; Choo and Klug (1994) Proc. Natl. Acad. Sci. USA 91, 11163–11167; Choo and Klug (1994) Proc. Natl. Acad. Sci. USA 91, 11168–11172; Choo et al (1994) Nature 372, 642–645; Wu et al (1995) Proc. Natl. Acad. Sci USA 92, 344–348). These mutants can be incorporated into ZFHD1 to provide new composite DNA binding regions with novel nucleotide sequence specificities. Other DBDs may be similarly altered. If structural information is not available, general mutagenesis strategies can be used to scan the entire domain for desirable mutations: for example alanine-scanning mutagenesis (Cunningham and Wells (1989) Science 244, 1081–1085), PCR misincorporation mutagenesis (see eg. Cadwell and Joyce (1992) PCR Meth. Applic. 2, 28–33), and 'DNA shuffling' (Stemmer (1994) Nature 370, 389–391). These techniques produce libraries of random mutants, or sets of single mutants, that can then be readily searched by screening or selection approaches such as phage display.

In all these approaches, mutagenesis can be carried out directly on the composite DNA binding region, or on the individual subdomain of interest in its natural or other protein context. In the latter case, the engineered component domain with new nucleotide sequence specificity may be subsequently incorporated into the composite DNA binding region in place of the starting component. The new DNA binding specificity may be wholly or partially different from that of the initial protein: for example, if the desired binding specificity contains (a) subsite(s) for known DNA binding subdomains, other subdomains can be mutated to recognize adjacent sequences and then combined with the natural domain to yield a composite DNA binding region with the desired specificity.

Randomization and selection strategies may be used to incorporate other desirable properties into the composite DNA binding regions in addition to altered nucleotide recognition specificity, by imposing an appropriate in vitro selective pressure (for review see Clackson and Wells (1994) Trends Biotech. 12, 173–184). These include improved affinity, improved stability and improved resistance to proteolytic degradation.

The ability to engineer binding regions with novel DNA binding specificities permits composite DNA binding regions to be designed and produced to interact specifically with any desired nucleotide sequence. Thus a clinically interesting sequence may be chosen and a composite DNA binding region engineered to recognize it. For example, composite DNA binding region may be designed to bind chromosomal breakpoints and repress transcription of an otherwise activated oncogene (see Choo et al (1994) Nature 372, 642–645); to bind viral DNA or RNA genomes and block or activate expression of key viral genes; or to specifically bind the common mutated versions of a mutational hotspot sequence in an oncogene and repress transcription (such as the mutation of codon 21 of human ras), and analogously to bind mutated tumor supressor genes and activate their transcription.

Additionally, in optimizing chimeric proteins of this invention it should be appreciated that immunogenicity of a polypeptide sequence is thought to require the binding of peptides by MHC proteins and the recognition of the presented peptides as foreign by endogenous T-cell receptors. It may be preferable, at least in gene therapy applications, to alter a given foreign peptide sequence to minimize the probability of its being presented in humans. For example, peptide binding to human MHC class I molecules has strict requirements for cerain residues at key 'anchor' positions in the bound peptide: eg. HLA-A2 requires leucine, methionine or isoleucine at position 2 and leucine or valine at the C-terminus (for review see Stem and Wiley (1994) Structure 2,145–251). Thus in engineered proteins, this periodicity of these residues could be avoided.

15. Tissue-specific or Cell-type Specific Expression

It may be preferred in certain embodiments that the chimeric protein(s) of this invention be expressed in a cell-specific or tissue-specific manner. Such specificity of expression may be achieved by operably linig one ore more of the DNA sequences encoding the chimeric protein(s) to a cell-type specific transcriptional regulatory sequence (e.g. promoter/enhancer). Numerous cell-type specific transcriptional regulatory sequences are known which may be used for this purpose. Others may be obtained from genes which are expressed in a cell-specific manner.

For example, constructs for expressing the chimeric proteins may contain regulatory sequences derived from known genes for specific expression in selected tissues. Representative examples are tabulated below:

| tissue | gene | reference |
| --- | --- | --- |
| lens | γ2-crystallin | Breitman, M. L., Clapoff, S., Rossant, J., Tsui, L. C., Golde, L. M., Maxwell, I. H., Bernstin, A. (1987) Genetic Ablation: targeted expression of a toxin gene causes microphthalmia in transgenic mice. Science 238: 1563–1565 |
| | αA-crystallin | Landel, C. P., Zhao, J., Bok, D., Evans, G. A. (1988) Lens-specific expression of a recombinant ricin induces developmental defects in the eyes of transgenic mice. Genes Dev. 2: 1168–78 Kaur, S., Key, B., Stock, J., McNeish, J. D., Akeson, R., Potter, S. S. (1989) Targeted ablation of alpha-crystallin-synthesizing cells produces lens-deficient eyes in transgenic mice. Development 105: 613–619 |
| pituitary somatrophic cells | Growth hormone | Behringer, R. R., Mathews, L. S., Palmiter, R. D., Brinster, R.L. (1988) Dwarf mice produced by genetic ablation |

| tissue | gene | reference |
|---|---|---|
| | | of growth hormone-expressing cells. Genes Dev. 2: 453–461 |
| pancreas | Insulin-Elastase - acinar cell specific | Ornitz, D. M., Palmiter, R. D., Hammer, R. E., Brinster, R. L., Swift, G. H., MacDonald, R. J. (1985) Specific expression of an elastase-human growth-fusion in pancreatic acinar cells of transgeneic mice. Nature 131: 600–603 Palmiter, R. D., Behringer, R. R., Quaife, C. J., Maxwell, F., Maxwell, I. H., Brinster, R. L. (1987) Cell lineage ablation in transgeneic mice by cell-specific expression of a toxin gene. Cell 50: 435–443 |
| T cells | lck promoter | Chaffin, K. E., Beals, C. R., Wilkie, T. M., Forbush, K. A., Simon, M. I., Perlmutter, R. M. (1990) EMBO Journal 9: 3821–3829 |
| B cells | Immuno-globulin kappa light chain | Borelli, E., Heyman, R., Hsi, M., Evans, R. M. (1988) Targeting of an inducible toxic phenotype in animal cells. Proc. Natl. Acad. Sci. USA 85: 7572–7576 Heyman, R. A., Borrelli, E., Lesley, J., Anderson, D., Richmond, D. D., Baird, S. M., Hyman, R., Evans, R. M. (1989) Thymidine kinase obliteration: creation of transgenic mice with controlled immunodeficiencies. Proc. Natl. Acad. Sci. USA 86: 2698–2702 |
| Schwann cells | $P_0$ promoter | Messing, A., Behringer, R. R., Hammang, J. P. Palmiter, RD, Brinster, RL, Lemke, G., P0 promoter directs espression of reporter and toxin genes to Schwann cells of transgenic mice. Neuron 8: 507–520 1992 |
| | Myelin basic protein | Miskimins, R. Knapp, L., Dewey, MJ, Zhang, X. Cell and tissue-specific expression of a heterologous gene under control of the myelin basic protein gene promoter in trangenic mice. Brain Res Dev Brain Res 1992 Vol 65: 217–21 |
| spermatids | protamine | Breitman, M. L, Rombola, H., Maxwell, I. H., Klintworth, G. K., Bernstein, A. (1990) Genetic ablation in transgenic mice with attenuated diphtheria toxin A gene. Mol. Cell. Biol. 10: 474–479 |
| lung | Lung surfacant gene | Ornitz, D. M., Palmiter, R. D., Hammer, R. E., Brinster, R. L., Swift, G. H., MacDonald, R. J. (1985) Specific expression of an elastase-human growth fusion in pancreatic acinar cells of transgeneic mice. Nature 131: 600–603 |
| adipocyte | P2 | Ross, S. R, Braves, RA, Spiegelman, BM Targeted expression of a toxin gene to adipose tissue: transgenic mice resistant to obesity Genes and Dev 7: 1318–124 1993 |
| muscle | myosin light chain | Lee, KJ, Ross, RS, Rockman, HA, Harris, AN, O'Brien, TX, van-Bilsen, M., Shubeita, HE, Kandolf, R., Brem, G., Prices et al J. Biol. Chem. 1992 Aug 5, 267: 15875–85 |
| | Alpha actin | Muscat, GE., Perry, S., Prentice, H. Kedes, L. The human skeletal alpha-actin gene is regulated by a muscle-specific enhancer that binds three nuclear factors. Gene Expression 2, 111–26, 1992 |
| neurons | neuro-filament proteins | Reeben, M. Halmekyto, M. Alhonen, L. Sinervirta, R. Saarma, M. Janne, J. Tissue-specific expression of rat light neurofilament promoter-driven reporter gene in transgenic mice. BBRC 1993: 192: 465–70 |
| liver | tyrosine amino-transferase, albumin, | |
| | apolipo-proteins | |

Identification of Tissue Specific Promoters

To identify the sequences that control the tissue- or cell-type specific expression of a gene, one isolates a genomic copy of the selected gene including sequences "upstream" from the exons that code for the protein.

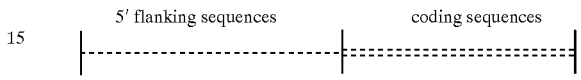

These upstream sequences are then usually fused to an easily detectable reporter gene like beta-galactosidase, in order to be able to follow the expression of the gene under the control of upstream regulatory sequences.

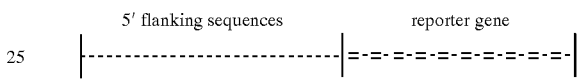

To establish which upstream sequences are necessary and sufficient to control gene expression in a cell-type specific manner, the complete upstream sequences are introduced into the cells of interest to determine whether the initial clone contains the control sequences. Reporter gene expression is monitored as evidence of expression.

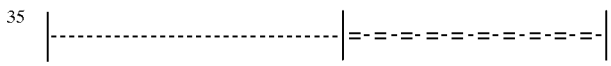

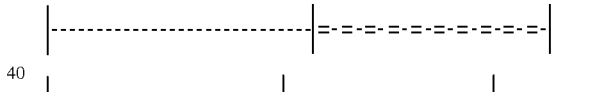

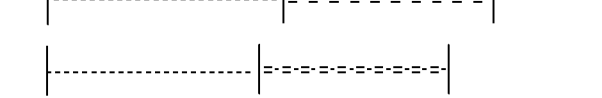

If these sequences contain the necessary sequences for cell-type specific expression, deletions (shown schematically above) may be made in the 5' flanking sequences to determine which sequences are minimally required for cell-type specific expression. This can be done by making transgenic mice with each construct and monitoring beta gal expression, or by first examining the expression in specific culture cells, with comparison to expression in non-specific cultured cells.

Several successive rounds of deletion analysis normally pinpoint the minimal sequences required for tissue specific expression. Ultimately, these sequences are then introduced into transgenic mice to confirm that the expression is only detectable in the cells of interest.

16. Applications

A. Constitutive Gene Therapy

Gene therapy often requires controlled high-level expression of a therapeutic gene, sometimes in a cell-type specific pattern. By supplying saturating amounts of an activating transcription factor of this invention to the therapeutic gene, considerably higher levels of gene expression can be obtained relative to natural promoters or enhancers, which are dependent on endogenous transcription factors. Thus, one application of this invention to gene therapy is the delivery of a two-transcription-unit cassette (which may reside on one or two plasmid molecules, depending on the delivery vector) consisting of (1) a transcription unit encoding a chimeric protein composed of a composite DNA-binding region of this invention and a strong transcription activation domain (e.g., derived from the VP16 protein, p65 protein, etc) and (2) a transcription unit consisting of the therapeutic gene expressed under the control of a minimal promoter carrying one, and preferably several, binding sites for the composite DNA-binding domain. Cointroduction of the two transcription units into a cell results in the production of the hybrid transcription factor which in turn activates the therapeutic gene to high level. This strategy essentially incorporates an amplification step, because the promoter that would be used to produce the therapeutic gene product in conventional gene therapy is used instead to produce the activating transcription factor. Each transcription factor has the potential to direct the production of multiple copies of the therapeutic protein.

This method may be employed to increase the efficacy of many gene therapy strategies by substantially elevating the expression of the therapeutic gene, allowing expression to reach therapeutically effective levels. Examples of therapeutic genes that would benefit from this strategy are genes that encode secreted therapeutic proteins, such as cytokines, growth factors and other protein hormones, antibodies, and soluble receptors. Other candidate therapeutic genes are disclosed in PCT/US93/01617.

B. Regulated Gene Therapy

In many instances, the ability to switch a therapeutic gene on and off at will or the ability to titrate expression with precision are essential to therapeutic efficacy. This invention is particularly well suited for achieving regulated expression of a target gene. Two examples of how regulated expression may be achieved are described. The first involves a recombinant transcription factor which comprises a composite DNA-binding domain, a potent transcriptional activation domain, and a regulatory domain controllable by a small orally-available ligand. One example is the ligand-binding domain of steroid receptors, in particular the domain derived from the modified progesterone receptor described by Wang et al, 1994, Proc Natl Acad Sci USA 91:8180–8184. In this example, the composite DNA binding domain of this invention is used in place of the GAL4 domain in the recombinant transcription factor and the target gene is linked to a DNA sequence recognized by the composite DNA binding domain. Such a design permits the regulation of a target gene by known anti-progestins such as RU486. The transcription factors described here greatly enhance the efficacy of this regulatory domain because of the enhanced affinity of the DNA-binding domain and the absence of background activity that arises from ligand-independent dimerization directed by the GAL4 domain in published constructs.

Another example involves a pair of chimeric proteins, a dimerizing agent capable of dimerizing the chimeras and a target gene construct to be expressed. The first chimeric protein comprises a composite DNA-binding region as described herein and one or more copies of one or more receptor domains (e.g. FKBP, cydophilin, FRB region of FRAP, etc.) for which a ligand, preferably a high-affinity ligand, is available. The second chimeric protein comprises an activation domain and one or more copies of one or more receptor domains (which may be the same or different than on the prior chimeric protein). The dimerizing reagent is capable of binding to the receptor (or "ligand binding") domains present on each of the chimeras and thus of dimerizing or oligomerizing the chimeras. DNA molecules encoding and directing the expression of these chimeric proteins are introduced into the cells to be engineered. Also introduced into the cells is a target gene linked to a DNA sequence to which the composite DNA-binding domain is capable of binding (if not already present within the cells). Contacting the engineered cells or their progeny with the oligomerizing reagent leads to regulated activity of the transcription factor and hence to expression of the target gene. In cases where the target gene and recognition sequence are already present within the cell, the activation domain may be replaced by a transcription repressing domain for regulated inhibition of expression of the target gene. The design and use of similar components is disclosed in PCT/US93/01617. These may be adapted to the present invention by the use of a composite DNA-binding domain, and DNA sequence encoding it, in place of the alternative DNA-binding domains as disclosed in the referenced patent document.

The dimerizing ligand may be administered to the patient as desired to activate transcription of the target gene. Depending upon the binding affinity of the ligand, the response desired, the manner of administration, the half-life, the number of cells present, various protocols may be employed. The ligand may be administered parenterally or orally. The number of administrations will depend upon the factors described above. The ligand may be taken orally as a pill, powder, or dispersion; bucally; sublingually; injected intravascularly, intraperitoneally, subcutaneously; Dy inhalation, or the like. The ligand (and monomeric antagonist compound) may be formulated using conventional methods and materials well known in the art for the various routes of administration. The precise dose and particular method of administration will depend upon i he above factors and be determined by the attending physician or human or animal healthcare provider. For the most part, the manner of administration will be determined empirically.

In the event that transcriptional activation by the ligand is to be reversed or terminated, a monomeric compound which can compete with the dimerizing ligand may be administered. Thus, in the case of an adverse reaction or the desire to terminate the therapeutic effect, an antagonist to the dimerizing agent can be administered in any convenient way, particularly intravascularly, if a rapid reversal is desired. Alternatively, one may provide for the presence of an inactivation domain (or transcriptional silencer) with a DNA binding domain In another approach, cells may be eliminated through apoptosis via signaling through Fas or TNF receptor as described elsewhere. See International Patent Applications PCT/US94/01617 and PCT/US94/08008.

The particular dosage of the ligand for any application may be determined in accordance with the procedures used for therapeutic dosage monitoring, where maintenance of a particular level of expression is desired over an extended period of times, for example, greater than about two weeks, or where there is repetitive therapy, with individual or repeated doses of ligand over short periods of time, with extended intervals, for example, two weeks or more. A dose of the ligand within a predetermined range would be given and monitored for response, so as to obtain a time-expression level relationship, as well as observing therapeutic response. Depending on the levels observed during the time period and the therapeutic response, one could provide a larger or smaller dose the next time, following the response. This process would be iteratively repeated until one obtained a dosage within the therapeutic range. Where the ligand is chronically administered, once the maintenance dosage of the ligand is determined, one could then do assays at extended intervals to be assured that the cellular system is providing the appropriate response and level of the expression product.

It should be appreciated that the system is subject to many variables, such as the cellular response to the ligand, the efficiency of expression and, as appropriate, the level of secretion, the activity of the expression product, the particular need of the patient, which may vary with time and circumstances, the rate of loss of the cellular activity as a result of loss of cells or expression activity of individual cells, and the like. Therefore, it is expected that for each individual patient, even if there were universal cells which could be administered to the population at large, each patient )would be monitored for the proper dosage for the individual.

C. Gene Therapy Endogenous Genes

This invention is adaptable to a number of approaches for gene therapy involving regulation of transcription of a gene which is endogenous to the engineered cells. These approaches involve the use of a chimeric protein as a transcription factor to actuate or increase the transcription of an endogenous gene whose gene product is beneficial or to inhibit the transcription of an endogenous gene whose gene product is excessive, disease-causing or otherwise determinental.

In one approach, a composite DNA-binding domain is designed or selected which is capable of binding to an endogenous nucleotide sequence linked to the endogenous gene of interest, e.g., a nucleotide sequence located within or in the vicinity of the promoter region or elsewhere in the DNA sequence flanking the endogenous gene's coding region. Alternatively, a known recognition sequence for a composite DNA-binding region may be introduced in proximity to a selected endogenous gene by homologous recombination to render the endogenous gene responsive to a corresponding chimeric transcription factor of this invention. See e.g. Gu et al., Science 265, 103–106 (1994). Constructs are made as described elsewhere which encode a chimeric protein containing the composite DNA-binding region and a transcription activation domain. Introduction into cells of the DNA construct permitting expression of the chimeric transcription factor leads to specific activation of transcription of the endogenous gene linked to the recognition sequence for the chimeric protein. Repression or inhibition of expression of the target gene may be effected using a chimeric protein containing the composite DNA-binding region, which may also contain an optional transcription inhibiting domain as described elsewhere. Again, as discussed elsewhere, the DNA construct may be designed to permit regulated expression of the chimeric protein, e.g. by use of an inducible promoter or by use of any of the regulatable gene therapy approaches which are known in the art. Likewise the construct may be under the control of a tissue specific promoter or enhancer, permitting tissue-specific or cell-type specific expression of the chimera and regulation of the endogenous gene. Finally, it should be noted that constructs encoding a pair of transcription factors containing ligand-binding domains permitting ligand-dependent function may be used in place of a single transcription factor construct.

D. Production of Recombinant Proteins and Viruses

Production of recombinant therapeutic proteins for commercial and investigational purposes is often achieved through the use of mammalian cell lines engineered to express the protein at high level. The use of mammalian cells, rather than bacteria or yeast, is indicated where the proper function of the protein requires post-translational modifications not generally performed by heterologous cells. Examples of proteins produced commercially this way include erythropoietin, tissue plasminogen activator, clotting factors such as Factor VIII:c, antibodies, etc. The cost of producing proteins in this fashion is directly related to the level of expression achieved in the engineered cells. Thus, because the constitutive two-transcription-unit system described above can achieve considerably higher expression levels than conventional expression systems, it may greatly reduce the cost of protein production. A second limitation on the production of such proteins is toxicity to the host cell: Protein expression may prevent cells from growing to high density, sharply reducing production levels. Therefore, the ability to tightly control protein expression, as described for regulated gene therapy, permits cells to be grown to high density in the absence of protein production. Only after an optimum cell density is reached, is expression of the gene activated and the protein product subsequently harvested.

A similar problem is encountered in the construction and use of "packaging lines" for the production of recombinant viruses for commercial (e.g., gene therapy) and experimental use. These cell lines are engineered to produce viral proteins required for the assembly of infectious viral particles harboring defective recombinant genomes. Viral vectors that are dependent on such packaging lines include retrovirus, adenovirus, and adeno-associated virus. In the latter case, the titer of the virus stock obtained from a packaging line is directly related to the level of production of the viral rep and core proteins. But these proteins are highly toxic to the host cells. Therefore, it has proven difficult to generate high-titer recombinant viruses. This invention provides a solution to this problem, by allowing the construction of packaging lines in which the rep and core genes are placed under the control of regulatable transcription factors of the design described here. The packaging cell line can be grown to high density, infected with helper virus, and transfected with the recombinant viral genome. Then, expression of the viral proteins encoded by the packaging cells is induced by the addition of dimerizing agent to allow the production of virus at high titer.

E. Use of Chimeric DBDs as Genomic Labelling Reagents

Chimeric proteins containing a composite DNA binding region can be used to label recognized nucleotide sequences in DNA molecules, including whole genome preparations such as chromosome spreads and immobilieed DNA matrices, that contain the specific recognition sites. This approach may be used for localizing these sequences to specific chromosomal regions after their introduction into genomic DNA, for example in a retroviral, vector for a gene therapy application. More generally, chimeric proteins containing a composite DNA binding region may be used as reagents to reveal the location of their nucleotide recognition sites for applications such as gene mapping, where they may be used as cytogenetic mark xs. DNA binding by composite DNA binding regions may have advantages over techniques such as fluoresence in situ hybridization (FISH) in that shorter nucleotide sequences could be specifically recognized. These approaches require the chimeric protein to be labelled in a way, for example by tagging with an epitope such as glutathione-S-transferase (GST) or the haemagglutinin (HA) tag, that can be readily visualized, e.g. by immunological and colorimetric detection; by biotinylation followed by detection with streptavidin; or by fusion to a directly detectable moiety such as green fluorescent protein (GFP).

F. Biological Research

This invention is applicable to a wide range of biological experiments in which precise recognition of a target gene is desired. These include: (1) expression of a proteirr or RNA of interest for biochemical purification; (2) regulated expression of a protein or RNA of interest in tissue culture cells for the purposes of evaluating its biological function; (3) regulated expression of a protein or RNA of interest in transgenic animals for the purposes of evaluating its biological function; (4) regulating the expression of another regulatory protein that acts on an endogenous gene for the purposes of evaluating the biological function of that gene. Transgenic animal models and other applications in which the composite DNA-binding domains of this invention may be used include those disclosed in U.S. patent application Ser. Nos. 08/292,595 and 08/292,596 (filed Aug. 18, 1994).

G. Kits

This invention further provides kits useful for the foregoing applications. One such kit contains a first DNA sequence encoding a chimeric protein comprising a composite DNA binding region of this invention (and may contain additional domains as discussed above) and a second DNA sequence containing a target gene linked to a DNA sequence to which the chimeric protein is capable of binding. Alternatively, the second DNA sequence may contain a cloning site for insertion of a desired target gene by the practitioner. For regulatable applications, i.e., in cases in which the recombinant protein contains a composite DNA-binding domain and a receptor domain, the kit may further contain a third DNA sequence encoding a transcriptional activating domain and a second receptor domain, as discussed above. Such kits may also contain a sample of a dimerizing agent capable of dimerizing the two recombinant proteins and activating transcription of the target gene.

The following examples contain important additional information, exemplification and guidance which can be adapted to the practice of this invention in its various embodiments and the equivalents thereof. The examples are offered my way illustration and not by way limitation.

EXAMPLES

The following examples describe the design, construction and use of chimeric proteins containing a composite DNA-binding region, identification of a consensus nucleic acid sequence bound by the composite DNA-binding region, assessment of its binding specificity and demonstration of its in vivo activity. The teachings of references cited herein are hereby incorporated by reference.

Example 1

Computer Modeling

Computer modeling studies (PROTEUS and MOGLI) were used to visualize how zinc fingers might be fused to the Oct-1 homeodomain. The known crystal structures of the Zif268-DNA (Pavletich and Pabo, *Science* 251:809 (1991)) and Oct-1-DNA (Klemm, et al., *Cell* 77:21 (1994)) complexes were aligned by superimposing phosphates of the double helices in several different orientations. This study yielded two arrangements which appeared to be suitable for use in a chimeric protein.

Each model was constructed by juxtaposing portions of two different crystallographically determined protein-DNA complexes. Models were initially prepared by superimposing phosphates of the double helices in various registers and were analyzed to see how the polypeptide chains might be connected. Superimposing sets of phosphates typically gave root mean squared distances of 0.5–1.5 Å between corresponding atoms. These distance gave some perspective on the error limits involved in modeling, and uncertainties about the precise arrangements were one of the reasons for using a flexible linker containing several glycines.

In one alignment, the carboxyl-terminal region of zinc finger 2 was 8.8 Å away from the amino-terminal region of the homeodomain, suggesting that a short polypeptide linker could connect these domains. In this model, the chimeric protein would bind a hybrid DNA site with the sequence 5'-AAATNNTGGGCG-3' (SEQ ID NO.: 18). The Oct-1 homeodomain would recognize the AAAT subsite, zinc finger 2 would recognize the TGG subsite, and zinc finger 1 would recognize the GCG subsite. No risk of steric interference between the domains was apparent in this model.

The second plausible arrangement would also have a short polypeptide linker connecting zinc finger 2 to the homeodomain (a distance of less than 10 Å); however, the subsites are arranged so that the predicted binding sequence is 5'-CGCCCANNAAAT-3' (SEQ ID NO.: 19). This model was not explicitly used in the subsequent studies, although it is possible that the flexible linker will also allow ZFHD1 to recognize this site.

Example 2

Construction of a Chimeric Protein

The design strategy was tested by construction of a chimeric protein, ZFHD1, that contained fingers 1 and 2 of Zif268, a glycine-glycine-arginine-arginine linker, and the Oct-1 homeodomain (FIG. 1A). A fragment encoding Zif268 residues 333–390 (Christy et al., *Proc. Natl. Acad. Sci. USA* 85:7857 (1988)), two glycines and the Oct-1 residues 378–439 (Sturm et al., *Genes & Development* 2:1582 (1988)) was generated by polymerase chain reaction, confirmed by dideoxysequencing, and cloned into the BamHI site of pGEX2T (Pharmacia) to generate an in-frame fusion to glutathione S-transferase (GST). The GST-ZFHD1 protein was expressed by standard methods (Ausubel et al., Eds., CURRENT PROTOCOLS IN MOLECULAR BIOLOGY (John Wiley & Sons, New York, 1994), purified on Glutathione Sepharose 4B (Pharmacia) according to the manufacturer's protocol, and stored at −80° C. in 50 mM Tris pH 8.0, 100 mM KCl, and 10% glycerol. Protein concentration was estimated by densitometric scanning of coomassie-stained SDS PAGE-resolved proteins using bovine serum albumin (Boehringer-Mannheim Biochemicals) as standard. The DNA-binding activity of this chimeric protein was determined by selecting binding sites from a random pool of oligonucleotides.

Example 3

Consensus Binding Sequences

The probe used for random binding site selection contained the sequence 5'-GGCTGAGTCTGAACGGATCCN$_{25}$CCTCGAG ACTGAGCGTCG-3' (SEQ ID NO.: 22). Four rounds of selection were performed as described in Pomerantz and Sharp, *Biochemistry* 33:10851 (1994), except that 100 ng poly[d(I-C)]/poly[d(I-C)] and 0025% Nonidet P40 were included in the binding reaction. Selections used 5 ng randomized DNA in the first round and approximately 1 ng in subsequent rounds. Binding reactions contained 6.4 ng of GST-ZFHD1 in round 1, 1.6 ng in round 2,0.4 ng in round 3 and 0.1 ng in round 4.

After four rounds of selection, 16 sites were cloned and sequenced (SEQ ID NOS.: 1–16, FIG. 1B). Comparing these sequences revealed the consensus binding site 5'-TAATTANGGGNG -3' (SEQ ID NO.: 17). The 5' half of this consensus, TAAFTA, resembled a canonical homeodomain binding site TAATNN (Laughon, (1991)), and matched the site (TAATNA) that is preferred by the Oct-1 homeodomain in the absence of the POU-specific domain (Verrijzer et al., *EMBO J.* 11:4993 (1992)). The 3' half of the consensus, NGGGNG, resembled adjacent binding sites for fingers 2 (TGG) and 1 (GCG) of Zif268. The guanines were more tightly conserved than the other positions in these zinc finger subsiies, and the crystal structure shows that these are the positions of the critical side chain-base interactions (Pavletich and Pabo (1991)).

The consensus sequence ZFHD1 was determined (5'-TAATTANGGGNG-3', SEQ ID NO.: 17), but because of the internal symmetry of the TAATTA subsite this sequence was consistent with the homeodomain binding in either of two orientations (FIG. 1C, compare mode 1 and mode 2). The second arrangement (FIG. 1C, mode 2), in which the critical TAAT is on the other strand and directly juxtaposed with the zinc finger (TGGGCG) subsites, was considered unlikely since modeling suggested that this arrangement required a linker to span a large distance between the carboxyl-terminal region of finger 2 and the amino-terminal region of the homeodomain.

To determine how the homeodomain binds to the TAATTA sequence in the 5' half of the consensus, ZFHD1 was tested for binding to probes (5'-TAATGATGGGCG-3', SEQ ID NO.: 21, and 5'-TCATTATGGGCG-3', SEQ ID NO.: 23) designed to distinguish between these orientations. ZFHD1 bound to the 5'-TAATQATGGGCG3' SEQ ID NO. 21 probe with a dissociation constant of 8.4×10$^{-10}$ M, and preferred this probe to the 5'-TCATTATGGGCG-3' SEQ ID NO. 23 probe by a factor of 33. This suggests that the first four bases of the consensus sequence form the critical TAAT subsite that is recognized by is the homeodomain and that ZFHD1 binds as predicted in the model shown in mode 1 of FIG. 1C.

Example 4

Novel Specificity

ZFHD1, the Oct-1 POU domain (containing a homeodomain and a POU-specific domain, Pomerantz et al., *Genes & Development* 6:2047 (1992)) and the three zinc fingers of Zif268 (obtained from M. Elrod-Erickson) were compared for their abilities to distinguish among the Oct-1 site 5'-ATGCAAATGA-3' (SEQ ID NO.: 20), the Zif268 site 5'-GCGTGGGCG-3' and the hybrid binding site 5'-TAATGATGGGCG3' (SEQ ID NO.: 21). DNA-binding reaction contained 10 mM Hepes (pH 7.9), 0.5 mM EDTA, 50 mM KCL, 0.75 mM DTT, 4% Ficoll-400, 300 μg/ml of bovine serum albumin, with the appropriate protein and binding site in a total volume of 10 μl. The concentration of binding site was always lower than the apparent dissociation constant by at least a factor of 10. Reactions were incubated at 30° C. for 30 minutes and resolved in 4% nondenaturing polyacrylaride gels. Apparent dissociation constants were determined as described in Pomerantz and Sharp, *Biochemistry* 33:10851 (1994). Probes were derived by cloning the following fragments into the Kpn I and Xho I sites of pBSKII+ (Stratagene) and excising the fragment with Asp718 and Hind III:

5'-CCTCGAGGTCATTATGGGCGCTAGGTACC-3' (SEQ ID NO.: 24).

5'-CCTCGAGGCGCCATTCATTACTAGGTACC-3' (SEQ ID NO.: 25).

5'-CCTCGAGGCGCCACGCCCTAGGTACC-3' (SEQ ID NO.: 26).

5'-CCTCGAGGTCATTTGCATACTAGGTACC-3' (SEQ ID NO.: 27).

Figure 2B:
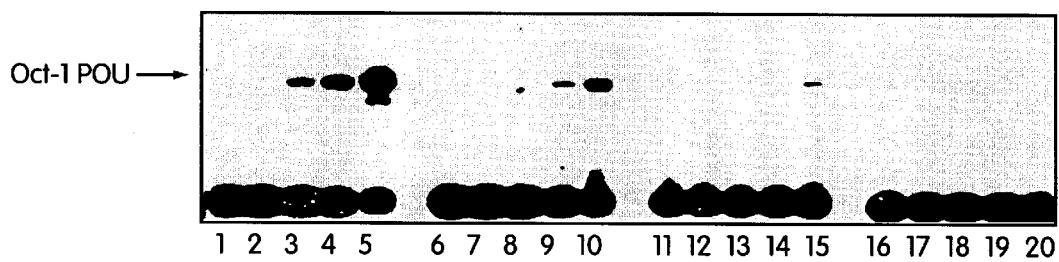
Figure 2C:
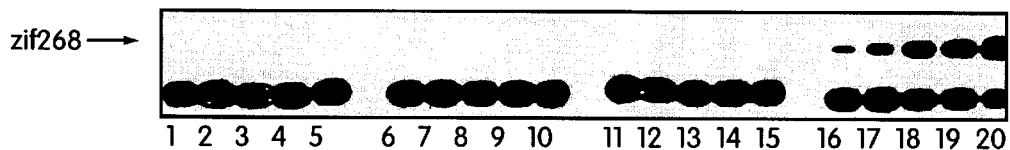

The GST-ZFHD1 protein was titrated into DNA-binding reactions containing the probes listed at the top of each set of lanes in FIG. 2. Lanes 1, 6, 11 and 16 contained the protein at 9.8×10$^{-11}$ M, and protein concentration was increased in 3-fold increments in subsequent lanes of each set. The chimeric protein ZFHD1 preferred the optimal hybrid site to the octamer site by a factor of 240 and did not bind to the Zif site.

The Oct-1-POU protein was titrated into DNA-binding reactions as with ZFHD1, but lanes 1, 6, 11 and 16 contained the protein at 2.1×10$^{-12}$ M. The POU domain of Oct-1 bound to the octamer site. with a dissociation constant of 1.8 ×10–10 M, preferring this site to the hybrid sequences by factors of 10 and 30, and did not bind to the Zif site.

A peptide containing Zif fingers 1, 2 and 3 was titrated into DNA-binding reactions as with ZFHD1 and the Oct-1-POU protein with lanes 1, 6, 11 and 16 containing the peptide at 3.3×10$^{-11}$ M. The three fingers of Zif268 bound to the Zif site with a dissociation constant of 3.3×10$^{-10}$ M, and did not bind to the other three sites. These experiments show that ZFHD1 binds tightly and specifically to the hybrid site and displayed DNA-binding specificity that was clearly distinct from that of either of the original proteins.

Example 5 in vivo Activity

ZFHD1 was fused to a transcriptional activation domain, and transfection experiments were used to determine whether the novel DNA-binding protein could function in vivo. An expression plasmid encoding ZFHD1 fused to the carboxyl-terminal 81 amino acids of the Herpes Simplex Virus VP16 protein (ZFHD1-VP16) was co-transfected into 293 cells with reporter constructs containing the SV40 promoter and the firefly luciferase gene (FIG. 3). The 293 cells were co-transfected with 5 μg of reporter vector, 10 μg of expression vector, and 5 μg of pCMV-hGH used as an internal control. The reporter vectors contained two tandem copies of either the ZFHD1 site (TAATGATGGGCG SEQ ID NO. 21), the Oct-1 site (ATGCAAATGA SEQ ID NO. 20), the Zif site (GCGTGGGCG) or no insert.

The ZFHD1-VP16 expression vector was constructed by cloning a fragment encoding ten amino acid polypeptide epitope MYPYDVPDYA; ZFHD1; and VP16 residues 399–479 (Pellett et al., *Proc. Natl. Acad. Sci. USA* 82:5870

(1985)) into the Not I and Apa I sites of Rc/CMV (Invitrogen). Reporter vectors were constructed by cloning into the Xho I and Kpn I sites of pGL2-Promoter (Promega) the following fragments:
5'-GGTACCAGTATGCAAATGACTAGCAGTATGCAAA TGACCTCGAG-3' (SEQ ID NO.: 28).
5'-GGTACCAGGCGTGGGCGCTGCAGGCGTGGGCGCCT CGAG-3' (SEQ 10 NO.: 29).
5'-GGTACCAGTAATGATGGGCGCTGCAG TAATGATGGGCGCCTCGAG-3' (SEQ ID NO.: 30).

The 293 cells were transfected using calcium phosphate precipitation with a glycerol shock as described in Ausubel et al., Eds., *Current Protocols in Molecular Biology* (John Wiley & Sons, New York, (1994). Quantitation of hGH production was performed using the Tandem-R HGH Immunoradiometric Assay (Hybritech Inc., San Diego, Calif.) according to the manufacturer's instructions. Cell extracts were made 48 hours after transfection and luciferase activity was determined using 10 µl of 100 µl total extract/100 an plate and 100 µl of Luciferase Assay Reagent (Promega) in a ML2550 Luminometer (Dynatech Laboratories, Chantilly, Va.) using the enhanced flash program and integrating for 20 seconds with no delay. The level of luciferase activity obtained, normalized to hGH production, was set to 1.0 for the co-transfection of Rc/CMV with the no-insert reporter pGL2-Promoter.

To determine whether the chimeric protein could specifically regulate gene expression, reporter constructs containing two tandem copies of either the ZFHD1 site 5-TAATGATGGGCG-3' (SEQ ID NO. 21), the octamer site 5'-ATGCAAATGA-3' (SEQ. ID NO. 20) or the Zif site 5'-GCGTGGGCG-3' inserted upstream of the SV40 promoter were tested. When the reporter contained two copies of the ZFHD1 site, the ZFHD1-VP16 protein stimulated the activity of the promoter in a dose-dependent manner. Furthermore, the stimulatory activity was specific for the promoter containing the ZFHD1 binding sites. At levels of protein which stimulated this promoter by 44fold, no stimulation above background was observed for promoters containing the octamer or Zif sites. Thus, ZFHD1 efficiently and specifically recognized its target site in vivo.

Example 6

Additional Examples

The following additional examples illustrate chimeric proteins containing the composite DNA-binding domain ZFHD1 together with various other domains, and the use of these chimeras in constitutive and ligand-dependent transcriptional activation.

A. Plasmids pCGNNZFHD1

An expression vector for directing the expression of ZFHD1 coding sequence in mammalian cells was prepared as follows. Zif268 sequences were amplified from a cDNA done by PCR using primers 5'Xba/Zif and 3'Zif+G. Oct1 homeodomain sequences were amplified from a cDNA c one by PCR using primers 5'Not Oct HD and Spe/Bam 3'Oct. The Zif268 PCR fragment was cut with XbaI and NotI. The OctI PCR fragment was cut with NotI and BamHI. Both fragments were ligated in a 3-way ligation between the XbaI and BamHI sites of pCGNN (Attar and Gilman, 1992) to make pCGNNZFHD1 in which the cDNA insert is under the transcriptional control of human CMV promoter and enhancer sequences and is linked to the nuclear localization sequence from SV40 T antigen. The plasmid pCGNN also contains a gene for ampicillin resistance which can serve as a selectable marker.

pCGNNZFHD1-p65

An expression vector for directing the expression in mammalian cells of a chimeric transcription factor containing the composite DNA-binding domain, ZFHD1, and a transcription activation domain from p65 human) was prepared as follows. The sequence encoding the C-terminal region of p65 containing the activation domain (amino acid residues 450–550) was amplified from pCGN-p65 using primers p65 5' Xba and p65 3' Spe/Bam. The PCR fragment was digested with Xba1 and BamH1 and ligated between the the Spe1 and BamH1 sites of pCGNN ZFHD1 to form PCGNN ZFHDp65AD.

The P65 transcription activation sequence contains the following linear sequence: CTGGGGGCCTTGCTTG-GCAACAGCACAGACCCAGCTGTGTTCA-CAGACCTGGCATCCGTCGACAACTC-CGAGTTTCAGCAGCTGCTGAACCAGGGCATACCTG TGGCCCCCCACACAACTGAGCCCATGCT-GATGGAGTACCCTGAGGCTATAACTCGC-CTAGTGACAGGGCCCAGAGGC-CCCCCGACCCAGCTCCTGCTCCACTGGGGGCCCCG GGGCTCCCCAATGGCCTCCTTTCAG-GAGATGAAGACTTCTCCTCCATTGCGGA-CATGGACTTCTCAGCCCTGCTGAGTCA-GATCAGCTCC (SEQ ID NO. 34)

pCGNNZFHD1-FKBPx3

An expression vector for directing the expression of ZFHD1 linked to three tandem repeats of human FKBP was prepared as follows. Three tandem repeats of human FKBP were isolated as an XbaI-BamHI fragment from pCGNNF3 and ligated between the Spe1 and BamHI sites of pCGN-NZFHD1 to make pCGNNZFHD1 -FKBPx3 (ATCC Accession No. 97399).

pZHWTx8SVSEAP

A reporter gene construct containing eight tandem copies of a ZFHD1 binding site (Pomerantz et al., 1995) and a gene encoding secreted alkaline phosphatase (SEAP) was prepared by ligating the tandem ZFHD1 binding sites between the Nhe1 and BglII sites of SEAP-Promoter Vec or (Clontech) to form pZHWTx8SVSEAP. The ZHWTx 8SEAP reporter contains two copies of the following sequence in tandem:
CTAGCTAATGATGGGCGCTCGAGTAAT-GATGGGCGGTCGACTAAT-GATGGGCGCTCGAGTAATGATGGGCGT (SEQ ID NO. 35)

ZFHD1 binding sites are underlined.

pCGNN F1 and F2

One or two copies of FKBP12 were amplified from pNF3VE using primers FKBP 5' Xba and FKBP 3' Spe/Bam. The PCR fragments were digested with Xba1 and BamH1 and ligated between the Xba1 and BamH1 sites of pCGNN vector to make pCGNN F1 or pPCGNN F2. pCGNNZFHD1-FKBPx3 can serve as an alternate source of the FKBP cDNA.

pCGNN F3

A fragment containing two tandem copies of FKBP was excised from pCGNN F2 by digesting with Xba1 and BamH1. This fragment was ligated between the Spe1 and BamH1 sites of pCGNN F1.

pCGNN F3VP16

The C-terminal region of the Herpes Simplex Virus protein, VP16 (AA 418–490) containing the activation domain was amplified from pCG-Gal4VP16 using primers VP16 5' Xba and VP16 3' Spe/Bam. The PCR fragment was digested with Xba1 and BamH1 and ligated between the Spe1 and BamH1 sites of pCGNN F3 plasmid.

pCGNN F3p65

The Xba1 and BamH1 fragment of p65 containing the activation domain was prepared as described above. This fragment was ligated between the Spe1, and BamH1 sites of pCGNN F3.

B. Primers

| Name | Sequence | |
|---|---|---|
| 5'Xba/Zif | 5'ATGCTCTAGAGAACGCCCATATGCTTGCCCT | (SEQ ID NO:36) |
| 3'Zif+G | 5'ATGCGCGGCCGCCGCCTGTGTGGGTGCGGATGTG | (SEQ ID NO:37) |
| 5'Not OctHD | 5'ATGCGCGGCCGCAGGAGGAAGAAACGCACCAGC | (SEQ ID NO:38) |
| Spe/Bam 3'Oct | 5'GCATGGATCCGATTCAACTAGTGTTGATTCTTTTTTCTTTCTGGCGGCG | (SEQ ID NO:39) |
| FKBP 5'Xba | 5'TCAGTCTAGAGGAGTGCAGGTGGAAACCAT | (SEQ ID NO:40) |
| FKBP 3'Spe/Bam | 5'TCAGGGATCCTCAATAACTAGTTTCCAGTTTTAGAAGCTC | (SEQ ID NO:41) |
| VP16 5'Xba | 5'ACTGTCTAGAGTCAGCCTGGGGGACGAG | (SEQ ID NO:42) |
| VP16 3'Spe/Bam | 5'GCATGGATCCGATTCAACTAGTCCCACCGTACTCGTCAATTCC | (SEQ ID NO:43) |
| P65 5'Xba | 5'ATGCTCTAGACTGGGGGCCTTGCTTGGCAAC | (SEQ ID NO:44) |
| p65 3'Spe/Bam | 5'GCATGGATCCGCTCAACTAGTGGAGCTGATCTGACTCAG | (SEQ ID NO:45) |

C. Dimerizing Agent

FK1012 consists of two molecules of the natural product FK506 covalently joined to one another by a synthetic linker and can be prepared from FK506 using published procedures. See e.g. PCT/US94/01617 and Spencer et al, 1993. FK1012 is capable of binding to two FKBP domains and functioning as a dimerizing agent for FKBP-containing chimeric proteins.

(i) ZFHD1-p65 and ZFHD1-VP16 Chimeric Proteins Activate Transcription of a Target Gene Linked to a Nucleotide Sequence Containing ZFHD1 binding sites HT1080 cells were grown in MEM (GIBCO BRL) supplemented with 10% Fetal Bovine Serum. Cells in 35 mm dishes were transiently transfected by lipofection as follows: 10, 50, 250 ng of ZFHD-activation domain fusion plasmids together with 1 µg of pZHWTx89iVSEAP plasmid DNA were added to a microfuge tube with pUC118 plasmid to a total of 2.5 µg DNA per tube. The DNA in each tube was then mixed with 20 µg lipofectamine in 200 µl OPJ0 E (GIBCO BRL). The DNA-lipofectamine mix was incubated at room temperature for 20 min. Another 800 µl of OPI-TIMEM was added to each tube, mixed and added to HT1080 cells pre piously washed with 1 ml DMEM (GIBCO BRL). The cells were incubated at 37° C. for 5 hrs. At this time, the DNA-lipofectamine media was removed and the cells were refed with 2 ml MEM containing 10% Fetal Bovine Serum. After 24 hrs incubation at 37° C., 20 µl of media was removed and assayed for SEAP activity as described (Spencer et al., 1993).

Results

Figure 4A:
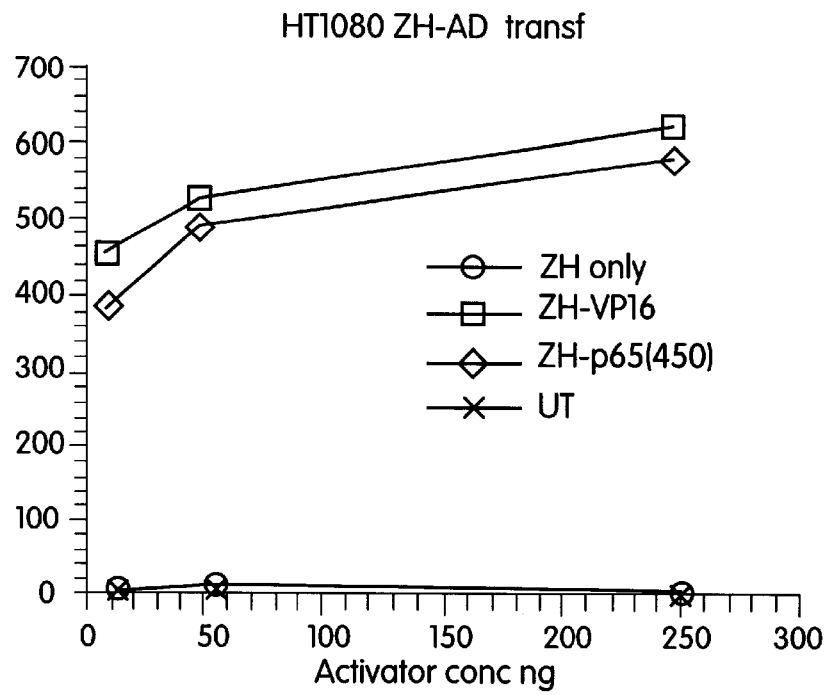
FIG. 4. Panel A illustrates data demonstrating that fusion proteins containing ZFHD1 linked to either a VP16 or p65 transcription activation domain activate transcription of a gene encoding secreted alkine phosphatase (SEAP) linked to ZFHD1 binding sites in HT1080 cells. Panel B illustrates data demonstrating that fusion proteins containing three copies of the FKBP domain joined to the VP16 or p65 activation domains support FK1012-dependent transcription of a reporter gene (secreted alkaline phosphatase) linked to a binding site for the ZFHD1 composite DNA-binding domain present in the ZFHD1-FKBP(×3) fusion protein. Panel C illustrates data from an analogous experiment using a wholly synthetic dimerizer in place of FK1012.

Both ZFHD1-VP16 and ZFHD1-p65 support transcriptional activation of a gene encoding SEAP linked to ZFHD1 binding sites. The results are shown in FIG. 4A.

(ii) FK1012-dependent Transcriptional Activation with ZFHD1-FKBPx3 and FKBPx3-VP16 or FKBPx3-p65

293 cells were grown in D-MEM (Gibco BRL) supplemented with 10% Bovine Calf Serum. Cells in 35mm dishes (2.5×10⁵ cells/dish) were transiently transfected with use of calcium phosphate precipitation (Ausubel et. al., 1994). Each dish received 375 ng pZHWTx8SVSEAP; 12ng pCGNNZFHD1-FKBPx3 and 25 ng pCGNNFKBPx3VP16 or pCGNNFKBPx3-p65. Following transfection, 2 ml fresh media was added and supplemented with FK1012 to the desired concentration. After a 24 hour incubation 100 ml aliquot of media was removed and assayed for SEAP activity as described (Spencer et. al., 1993).

Results

Figure 4B:
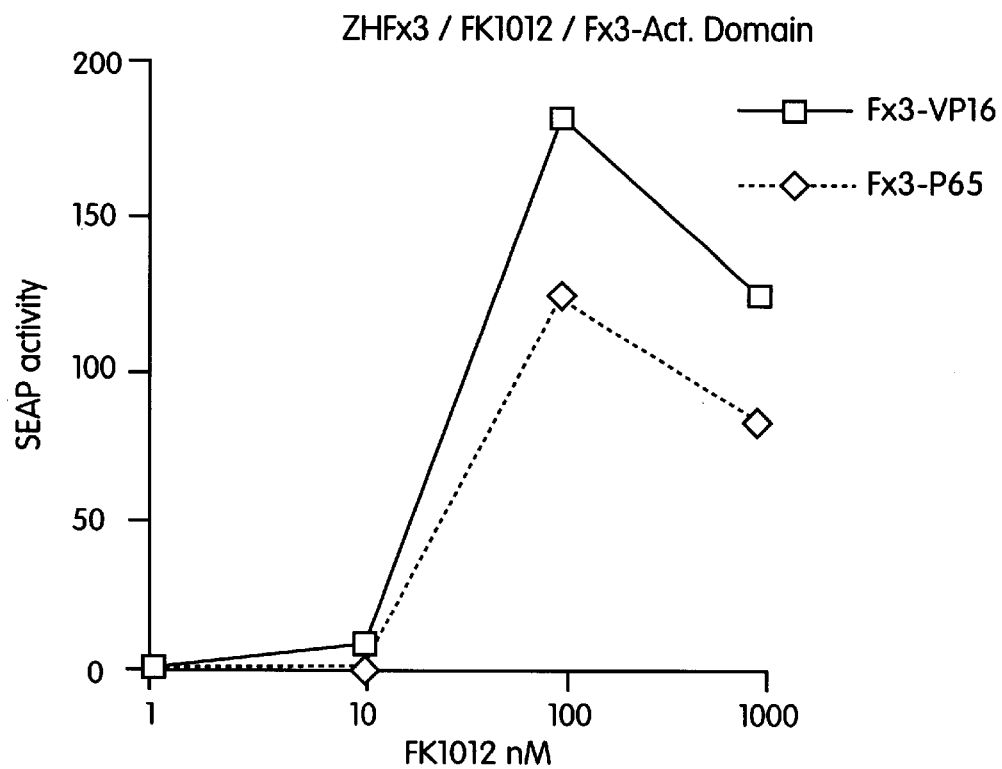

ZFHD1-FKBPx3 supports FK1012 dependent transcriptional activation in conjunction with FKBPx3-VP16 or FKBPx3-p65. Peak activation was observed at FK1012 concentration of 100 nM. See FIG. 4B.

(iii) Synthetic Dimerizer-dependent Transcriptional Activation with ZFHD1 -FKBPx3 and FKBPx3-VP16 or FKBPx 3-p65

An analgoous experiment was conducted using a wholly synthetic dimerizer in place of FK1012. Like FK1012, the synthetic dimerizer is a divalent FKBP-binder and is capable

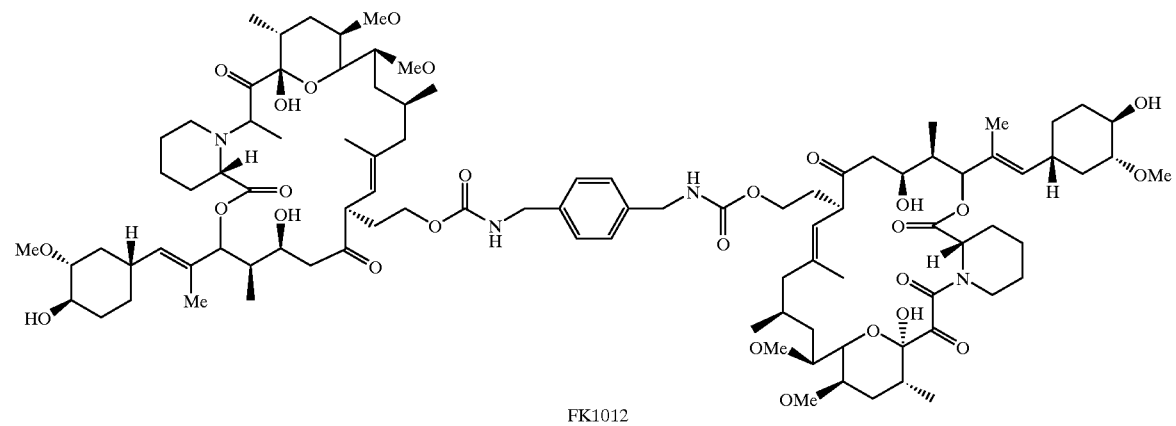

FK1012 of dimerizing chimeric proteins which contain FKBP domains. In this experiment, 293 cells were grown in DMEM supplemented with 10% Bovine Calf Serum. Cells in 10 cn dishes were transiently transfected by calcium phosphate precipitation (Natesan and Gilnan, 1995, *Mol. Cell Biol*, 15, 5975–5982). Each plate received 1 μg of pZHWTx8SVSEAP reporter, 50 ng pCGNNZFHD1-FKBP3×3, 50 ng pCGNNF3p65 or pCGNNF3VP16. Following transfection, 2 ml fresh media was added and supplemented with a synthetic dimerizer to the desired concentration. After 24 hrs, 100 μl of the media was assayed for SEAP activity as described (Spencer et al, 1993).

Results

Figure 4C:
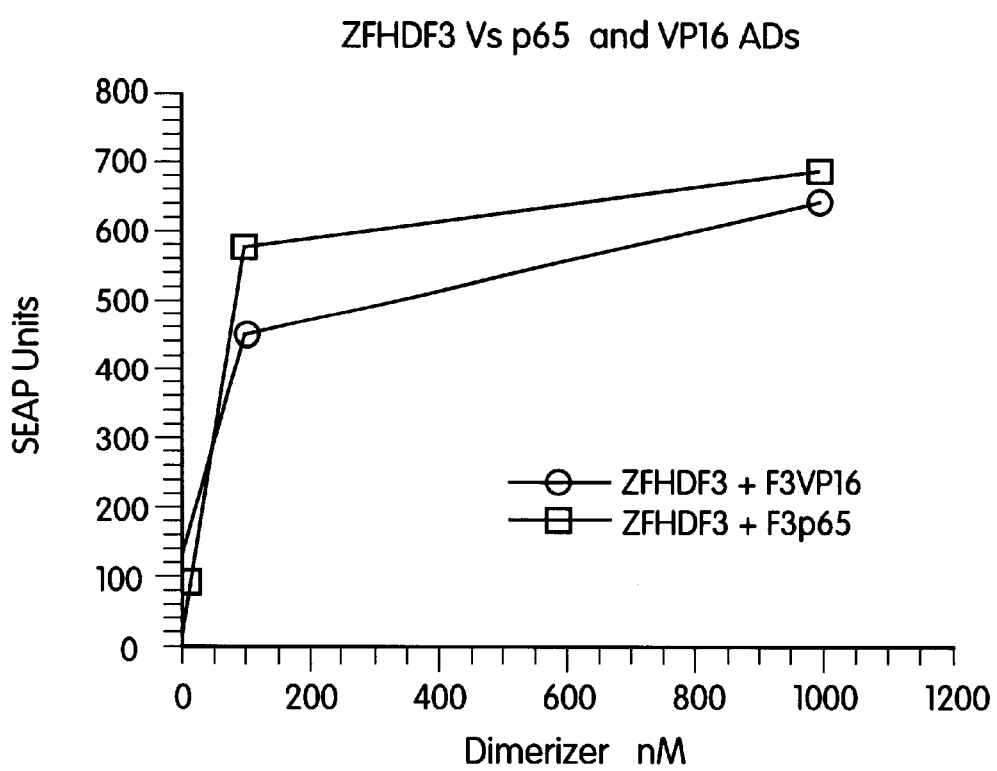

ZFHD1-FKBP×3 supports synthetic dimerizer-dependent transcriptional activation in conjunction with FKBP×3VP16 or FKBP×3p65. See FIG. 4C.

REFERENCES

1. Attar, R. M., and M. Z. Gilman 1992. *Mol. Cell. Biol.* 12:2432–2443
2. Ausubel, F. M. et al., Eds., 1994. CURRENT PROTOCOLS IN MOLECULAR BIOLOGY (Wiley, N.Y.)
3. Pomerantz, J. L., et al. 1995. *Science*. 267:93–96.
4. Spencer, D. M., et al. 1993. *Science*. 262:1019–1024.

Example 7

Rapamycin-dependent Transcriptional Activation with ZFHD1-FKBP×3 and FRAP-p65 in Whole Animals Using the approach described in Example 6, constructs were prepared encoding the ZFHD1-FKBP×3 fusion protein, a second fusion protein containing the FKBP:rapaymcin binding ("FRB") region of FRAP linked to the p65 activation domain, and a reporter cassette containing a gene encoding human growth hormone linked to multiple ZFHD1 binding sites. The natural product, rapamycin, forms a ternary complex with FKBP12 and FRAP. Similarly, rapamycin is capable of binding to one or more of the FKBP domains and FRAP FRB domains of the fusion proteins. The three constructs were introduced into HT1080 cells which were then shown to support rapamycin-dependent expression of the hGH gene in cell culture, analogously to the experiments described in Example 6.

2×10⁶ cells from the transfected HT1080 culture were administered to nu/nu mice by intramuscular injection. Following cell implantation, rapamycin was administered i.v. over a range of doses (from 10–10,000 μl /kg). Serum samples were collected from the mice 17 hours after rapamycin administration. Control groups consisted of mice that received no cells but 1.0 mg/kg rapamycin (i.v.) as well as mice that received the cells but no rapamycin.

Figure 5:
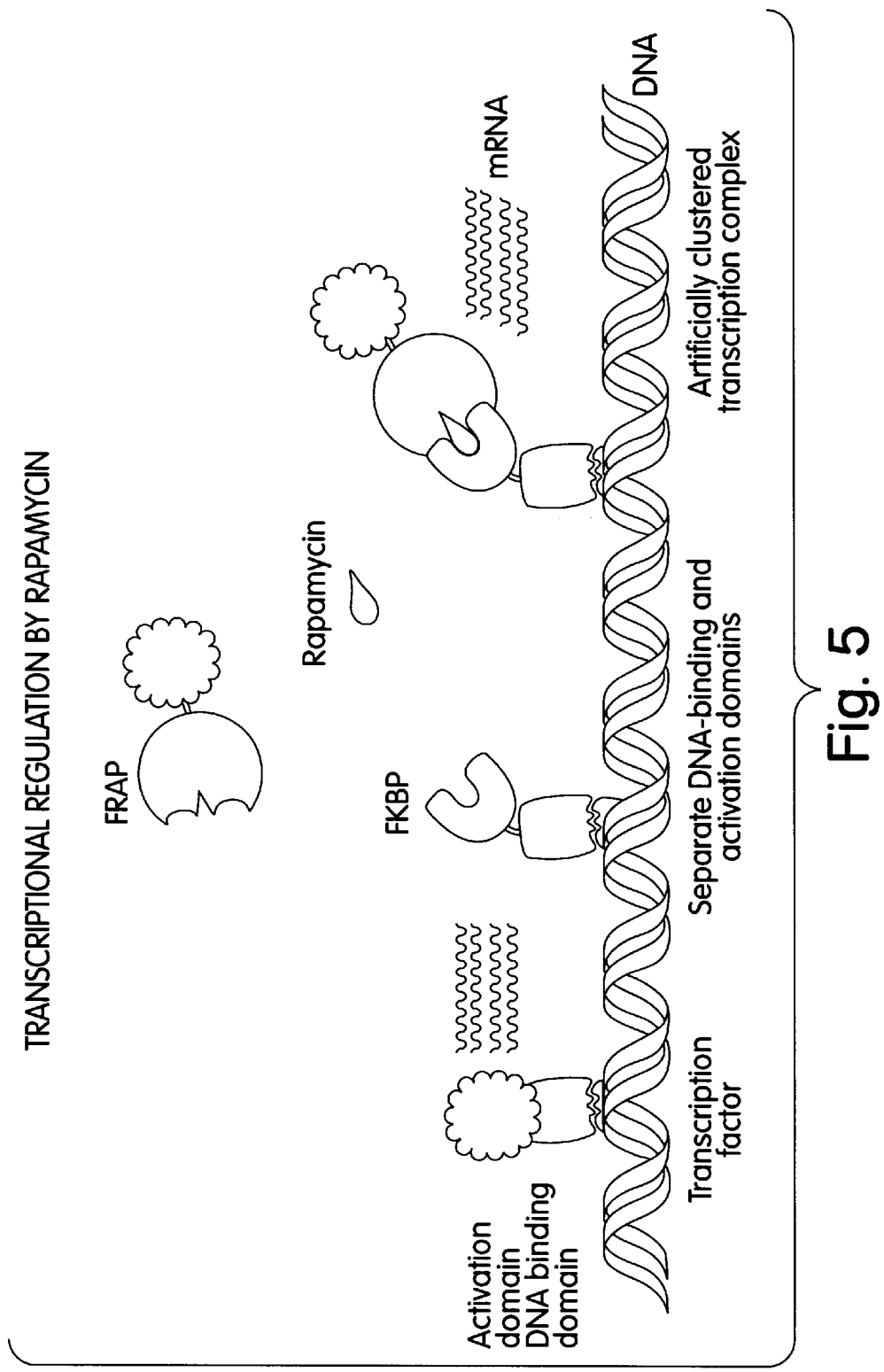
FIG. 5 illustrates in schematic form a chimeric transcription factor of this invention containing a composite DNA binding domain and a transcription activation domain, bound to its recognized DNA sequence. Also illustrated is a chimeric protein of this invention containing one or more FKBP domains, a cognate chimeric protein containing a FRAP FRB domain linked to a transcription activation domain, and a complex of those two chimeras formed in the presence of the dimerizer, rapamycin, resulting in the clustering of the transcriptional complex on a recognized DNA sequence.
Figure 6:
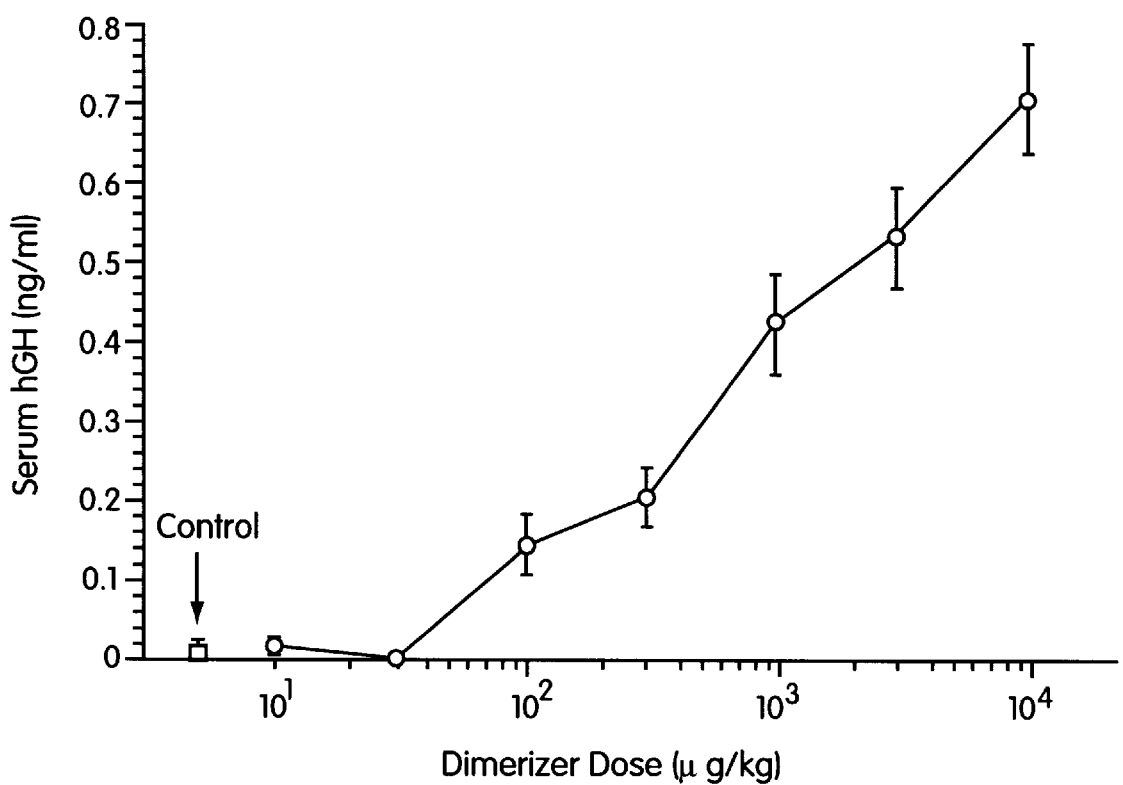
FIG. 6 illustrates data demonstrating functional dimerizer-dependent expression of an hGH target gene resulting from complexation of the ZFHD1-FKBP(×3) fusion protein to a FRAP FRB-p65 fusion protein and binding of the complex to a ZFHD1 binding site in engineered cells in whole animals. These data demonstrate that in vivo administration of a dimerizing agent can regulate gene expression in whole animals of secreted gene products from cells containing the fusion proteins and a responsive target gene cassette. Human cells ($2\times10^6$) transfected with plasmids encoding transcription factors ZFHD1-FKBP×3 and FRB-p65 and a target gene directing the expression of human growth hormone (hGH) were injected into the skeletal muscles of nu/nu mice. Mice were treated with the indicated concentration of rapamycin by tail vein injection. After 17 hours, serum hGH levels were determined by ELISA. Each point represents X±SEM (n=at least 5 per point). Control animals received either engineered cells without drug or drug ($10^3$ or $10^4$ μg/kg) without engineered cells.

Dose-responsive expression of hGH was observed (as circulating hGH) over the range of rapamycin doses administered. Neither control group produced measurable hGH. The limit of detection of the hGH assay is 0.0125 ng/ml. See FIG. 5.

These data show functional DNA binding of ZFHD1-FKBP(×3) to a ZFHD1 binding site in the context of dimerization with another fusion protein in whole animals. These data demonstrate that in vivo administration of a dimerizing agent can regulate gene expression in whole animals of secreted gene products from cells containing the fusion proteins and a responsive target gene cassette. We have previously demonstrated that a bolus hGH administration, either i.p. or iv., results in rapid hGH clearance with a half-life of less than 2 minutes and undetectable levels by 30 minutes. Therefore, the observed hGH secretion in this example appears to be a sustained phenomenon.

Example 8

FRAP FRB Constructs

This Example provides further background and information relevant to constructs encoding chimeric proteins containing an FRB domain derived from FRAP for use in the practice of this invention. The VP16-FRB construct described below is analogous to the p65FRB construct used Example 7.

Rapamycin is a natural product which binds to a FK506-binding protein, FKBP, to form a rapamycin:FKBP complex. That complex binds to the protein FRAP to form a ternary, [FKBP:rapamycin]:[FRAP], complex. The rapamycin-dependent association of FKBP12 and a 289 kDa mammalian protein termed FRAP, RAFT1 or RAPT1 and its yeast homologs DRR and TOR (hereafter referred to as "FRAP") have been described by several research groups. See e.g. Brown. et al, 1994, *Nature* 369:756–758, Sabatini et al, 1994, *Cell* 78:35–43, Chiu et al, 1994, *Proc. Natl. Acad. Sci. USA* 91:12574–12578, Chen et al, 1994, *Biochem. Biophys. Res. Comm.* 203:1–7, Kunz et al, 1993 *Cell* 73:585–596, Cafferkey et al, 1993 *Mol. Cell. Biol.* 13:6012–6023. Chiu et al, supra, and Stan et al, 1994, *J. Biol. Chem.* 269:32027–32030 describe the rapamycin-dependent binding of FKBP12 to smaller subunits of FRAP.

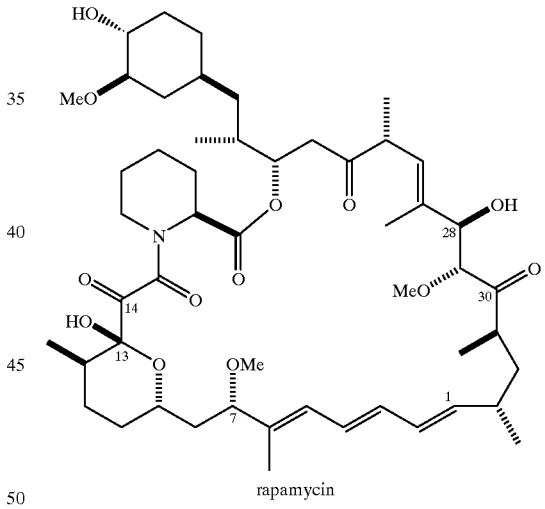

rapamycin

Construct Encoding FRAP Domain(s)-VP16 Transcriptional Activation Domain(s)-epitope Tag The starting point for assembling this construct was the eukaryotic expression vector pBJ5/NF1E, described in PCT/US94/01617. pBJ5 is a derivative of pCDL-SR (MCB 8,466–72) in which a polylinker containing 5' SacII and 3' EcoRI sites has been inserted between the 16S splice site and the poly A site. To construct pBJ5/NF1E a cassette was cloned into this polylinker that contained a Kozak sequence and start site, the coding sequence of the SV40 T antigen nuclear localization sequence (NLS), a single FKBP domain, and an epitope tag from the H. influenza haemagglutini protein (HA), flanked by restriction sites as shown below:

```
    Kozok            SV40 NLS                           FKBP (5')
         M  E  D  P  K  K  K  R  K  V  L  E  G  V  Q  V  E...
CCGCGGCCACCATGCTCGACCCTAAGAAGAAGAGAAAGGTACTCGAGGGCGTGCAGGTGGAG...
SocII         (X/S)                              XhoI FKBP(3')               HA(flu)tag
...L  L  K  L  E  V  D  Y  P  Y  D  V  P  D  Y  A  E  D  End           (SEQ ID NO:47)
...CTTCTAAAACTGGAAGTCGACTATCCGTACGACGTACCAGACTACGCACTCGACTAAGAATTC     (SEQ ID NO:46)
             SalI                                      (X/S)      EcoRI
``` where (X/S) denotes the result of a ligation event between the compatible products of digestion by XhoI and SalI, to produce a sequence that is cleavable by neither enzyme. Thus the XhoI and SalI sites that flank the FKBP coding sequence are unique.

The series of constructs encoding FRAP-VP16 fusions is assembled from pBJ5/NF1E in two steps: (i) the hoI-SaUl restriction fragment encoding FKBP is excised and replaced with fragments encompassing all or part of the coding sequence of human FRAP, obtained by PCR amplification, generating construct NR1E and relatives (where R denotes FRAP or a portion thereof; (ii) the coding sequence of the VP16 activation domain is cloned into the unique SalI site of these vectors to yield construct NRIV1E and relatives. At each stage additional manipulations are performed to generate constructs encoding multimers of the FRAP-derived and/or VP16 domains.

(i) Portions of human FRAP that include the region required for FRAP binding are amplified by PCR using a 5' primer that contains a XhoI site and a 3' primer that contains a SalI site. The amplified region can encode full-length FRAP (primers 1 and 4: fragment a); residues 2012 through 2144 (a 133 amino acid region that retains the ability to bind FKBP-rapamycin; see Chiu et al. (1994) Proc. Natl. Acad. Sci USA 91: 12574–12578)(primers 2 and 5: fragment b); or residues 2025 through 2114 (a 90 amino acid region that also retains this ability; see Chen et al. (1995) Proc. Natl. Acad. Sci. USA 92: 4947–4951)(primers 3 and 6: fragment c). The DNA is amplified from human cDNA or a plasmid containing the FRAP gene by standard methods, and the PCR product is isolated and digested with SalI and XhoI. Plasmid pBJ5/NF1E is digested with SalI and XhoI and the cut vector purified. The digested PCR products are ligated into the cut vector to produce the constructs NRa1E, NRb1E and NRc1E, where Ra, Rb and Rc denote the full-length or partial FRAP fragments as indicated above. The constructs are verified by DNA sequencing.

Multimers of the FRAP domains are obtained by isolating the Ra, Rb or Rc sequences from the NRa1E, NRb1E and NRc1E vectors as XhoI/SalI fragments and then ligating these fragments back into the parental construct linearized with XhoI. Constructs containing two, three or more copies of the FRAP domain (designated NRa2E, NRa3E, NRb2E, NRb3E etc) are identified by restriction or PCR analysis and verified by DNA sequencing.

```
5' ends of amplified products:
FRAP fragment a (full-length: primer 1)
         L  E  L  G  T  G  P  A  A              (SEQ ID NO:49)
     5' CGAGTCTCGAGCTTGGAACCGGACCTGCCGCC         (SEQ ID NO:48)
             XhoI FRAP fragment b (residues 2012–2144: primer 2)
            L  E  V  S  E  E  L  I  R           (SEQ ID NO:51)
     5' CGAGTCTCGAGGTGAGCGAGGAGCTGATCCGA         (SEQ ID NO:50)
             XhoI FRAP fragment c (residues 2025–2114: primer 3)
            L  E  E  M  W  H  E  G  L           (SEQ ID NO:53)
     5' CGAGTCTCGAGGAGATGTGGCATGAAGGCCTG         (SEQ ID NO:52)
             XhoI 3' ends of amplified products:
FRAP fragment a (full-length: primer 4)
         I  G  W  C  P  F  W  V  D              (SEQ ID NO:55)
     5' ATTGGCTGGTGCCCTTTCTGGGTCGACCGAGT         (SEQ ID NO:54)
     3' TAACCGACCACGGGAAAGACCCAGCTGGCTCA
                                         SolI FRAP fragment b (residues 2012–2144: primer 5)
         L  A  V  P  G  T  Y  V  D              (SEQ ID NO:57)
     5' TTGGCTGTGCCAGGAACATATGTCGACCGAGT         (SEQ ID NO:56)
     3' AACCGACACGGTCCTTGTATACAGCTGGCTCA
                                         SolI FRAP fragment c (residues 2012–2144: primer 6)
         F  R  R  I  S  K  Q  V  D              (SEQ ID NO:59)
     5' TTCCGACGAATCTCAAAGCAGGTCGACCGAGT         (SEQ ID NO:58)
     3' AAGGCTGCTTAGAGTTTCGTCCAGCTGGCTCA
                                         SolI
```

(ii) The VP16 transcriptional activation domain (amino acids 413–490) is amplified by PCR using a 5' primer (primer 7) containing a XhoI site and a 3' primer (primer 8) containing a SalI site. The PCR product is isolated, digested with SalI and XhoI, and ligated into plasmid pBJ5/NF1E digested with SalI and XoI to generate the intermediate NV1E. The construct is verified by restriction or PCR analysis and DNA sequencing. Multimerized VP16 domains are created by isolating the single VP16 sequence as a XhoI-SalU fragment from NV1E, and then ligating this fragment back into NV1E that is linearized with XhoI. This process generates constructs NV2E, NV3E and NV4E etc which can be identified by restriction or PCR analysis and verified by DNA sequencing.

```
5' end of PCR product:
           413
       L E A P P T D V        (SEQ ID NO:61)
5' CGACACTCGAGGCCCCCCCGACCGATGTC  (SEQ ID NO:60)
       XhoI
```

```
Oligonucleotides:
                                        (SEQ ID NO:48)
1    5'CGAGTCTCGAGCTTGGAACCGGACCTGCCGCC (SEQ ID NO:50)
2    5'CGAGTCTCGAGGTGAGCGAGGAGCTGATCCGA (SEQ ID NO:52)
3    5'CGAGTCTCGAGGAGATGTGGCATGAAGGCCTG (SEQ ID NO:54)
4    5'ACTCGGTCGACCCAGAAAGGGCACCAGCCAAT (SEQ ID NO:56)
5    5'ACTCGGTCGACATATGTTCCTGGCACAGCCAA (SEQ ID NO:58)
6    5'ACTCGGTCGACCTGCTTTGAGATTCGTCGGAA (SEQ ID NO:60)
7    5'CGACACTCGAGGCCCCCCCGACCGATGTC (SEQ ID NO:62)
8    5'CGACAGTCGACCCCACCGTACTCGTC
```

```
Sequence of representative final construct (NRc1V1E):
    Kozok           SV40 NLS                    FRAP(2025-2114)
         M  E  D  P  K  K  K  R  K  V  L  E  F  M  W  H  F...
CCGCGGCCACCATGCTCGACCCTAAGAAGAAGAGAAAGGTACTCGAGGAGATGTGGCATGAA...
SocII         (X/S)                             XhoI FRAP(2025-2114)      VP16(413-490)  ...VP16(413-490)
...R  I  S  K  Q  V  D  A  P  P  T  D    D  E  Y  G  G  V  D
...CGAATCTCAAAGCAGGTCGAGGCCCCCCCGACCGAT...GACGAGTACGGTGGGGTCGAC
                        (S/X)                          SalI HA(flu)tag
   Y  P  Y  D  V  P  D  Y  A  E  D  End
   TATCCGTACGACGTACCAGACTACGCACTCGACTAAGAATTC            (SEQ ID NO:65)
                            (X/S)        EcoRI           (SEQ ID NO:64)
```

```
                    -continued
3' end of PCR product:
           490
        D E Y G G V D             (SEQ ID NO:63)
5' GACGAGTACGGTGGGGTCGACTGTCG     (SEQ ID NO:62)
3' CTGCTCATGCCACCCCAGCTGACAGC
                SalI
```

The final constructs encoding fusions of portions of FRAP with VP16 are created by transferring the VP16 sequences into the series of FRAP-encoding vectors described in (i). XhoI-SaRl fragments encoding the 1, 2, 3 and 4 copies of the VP16 activation domains are generated by digestion of NV1E, NV2E, NV3E and NV4E. These fragments are then ligated into vectors NRa1E, NRb1E and NRc1E linearized with Sail, generating NRa1V1E, NRb1V1E, NRc1V1E, NRa1V2E, NRb1V2E, etc. Similarly, vectors encoding multiple copies of the FRAP domains are obtained by ligation of the same fragments into vectors NRa2E, NRa3E, NRb2E, NRb3E etc. All of these vectors are identified by restriction or PCR analysis and verified by DNA sequencing. Thus the final series of vectors encodes (from the N to the C terminus) a nuclear localization sequence, one more FRAP-derived domains fused N-terminally to one or more VP16 transcriptional ivation domains (contained on a single XhoI-SalI fragment), and an epitope tag.

Example 9

Constructs for Chimeric Proteins Containing Alternative Composite DNA-binding Regions The following DNA vectors were prepared containing recombinant DNA sequences encoding component DNA binding subdomains and composite DNA binding regions containing them.

Constructs.

All plasmids are constructed in pET-19BHA, a pET-19B based vector modified such that all expressed proteins contain an amino-terminal Histidine "Tag" for purification and an epitope tag for immunoprecipitation. pET-19B is a well-known vector for expression of heterologous proteins in E coli or in reticulocyte lysates.

Zinc Finger Constructs

All zinc finger sequences are derived from the human cDNA encoding SRE-ZBP (Attar, R. M. and Gilman, M. Z. 1992. *MCB* 12 2432–2443).

p19B2F: Contains SREZBP zinc fingers 6 and 7 (amino acids 328 to 410) fused in frame to the epitope tag in p19BHA. DNA encoding ZBP zinc fingers 6 and 7 was generated by PCR using primers 2F-Xba5' and ZNF-Spe/Bam (see below). The resulting fragment was cut with XbaI and BamHI and ligated between the XbaI and BamHI sites of pET-19BHA.

p19B4F: Contains SREZBP zinc fingers 4, 5, 6 and 7 (amino acids 300 to 410) fused in frame to the epitope tag in p19BHA. A DNA fragment encoding ZBP zinc fingers 4, 5, 6 and 7 was generated by PCR using primers 4F-Xba5' and ZNFSpe/Bam. The resulting fragment was cut with XbaI and BamHI and ligated between the XbaI and BamHI sites of pET-19BHA.

p9B7F: Contains SREZBP zinc fingers 1 to 7 (amino acids 216 to 410) fused in frame to the epitope tag in p19BHA. DNA encoding ZBP zinc fingers 1 to 7 was generated by PCR using primers 7F-Xba5' and ZNF-Spe/Bam. The resulting fragment was cut with XbaI and BamHI and ligated between the XbaI and BamHI sites of pET-19BHA.

p19BF1: Contains SREZBP zinc finger 1 (amino acids 204 to 241) fused in frame to the epiope tag in p19BHA. DNA encoding ZBP zinc finger 1 was generated by PCR using primers ZBPZF15' and ZBPZF13'. The resulting fragment was cut with XbaI and BamHI and ligated between the XbaI and BamHI sites of pET-19BHA.

p19BF123: Contains SREZBP zinc fingers 1, 2 and 3 (amino acids 204 to 297) fused in frame to the epitope tag in p19BHA. DNA encoding ZBP zinc fingers 1, 2 and 3 was generated by PCR using primers ZBPZF15' and ZBPZF33'. The resulting fragment was cut with XbaI and BamHI and ligated between the XbaI and BamHI sites of pET-19BHA.

Homeodomain Construct p19BHH: Contains the Phox1 homeodomain and flanking amino acids (amino acids 43 to 150 (Grueneberg et al. 1992. Science. 257: 1089–1095)) fused in frame to the epitope tag in pl9BHA. DNA encoding the Phox1 fragment was generated by PCR using primers Phox HH5' Primer and Phox HH Spe/Bam. The resulting fragment was cut with Xba1 and BamHI and ligated between the XbaI and BamHI sites of pET-19BHA.

Zinc Finger/Homeodomain Constructs p19B2FHH: Contains SREZBP zinc fingers 6 and 7 (amino acids 328 to 410) fused in frame to the epitope tag in p19BHA followed by the Phox1 homeodomain (amino acids 43 to 150). An XbaI-BamHI fragment from p19BHH containing sequences encoding the Phox1 homeodomain was ligated between the SpeI and BamHI sites of pl9B2F.

p19B4FHH: Contains SREZBP zinc fingers 4, 5, 6 and 7 (amino acids 300 to 410) fused in frame to the epitope tag in p19BHA followed by the Phox1 homeodomain (amino acids 43 to 150). An XbaI-BamHI fragment from p19BHH containing sequences encoding the Phox1 homeodomain was ligated between the SpeI and BamHI sites of p19B4F.

p19B7FHH: Contains SREZBP zinc fingers 1 to 7 (amino acids 216 to 410) fused in frame to the epitope tag in p19BHA followed by the Phox1 homeodomain (amino acids 43 to 150). An XbaI-BamHI fragment from p19BHH containing sequences encoding the Phox1 homeodomain was ligated between the SpeI and BamHI sites of p19B7F.

p19BZFlHH: Contains SREZBP zinc finger 1 (amino acids 204 to 241) fused in frame to the epitope tag in pl9BHA followed by the Phoxi homeodomain (amino acids 43 to 150). An XbaI-BamHI fragment from p19BHH containing sequences encoding the Phox1 homeodomain was ligated between the SpeI and BamHI sites of p19BZF1.

p19BZF123HH: Contains SREZBP zinc finger 1, 2 and 3 (amino acids 204 to 297) fused in frame to the epitope tag in p19BHA followed by the Phox1 homeodomain (amino acids 43 to 150). An XbaI-BamHI fragment from p19BHH containing sequences encoding the Phox1 homeodomain was ligated between the SpeI and BamHI sites of p19BZF123.

Homeodomain/Zinc Finger Constructs p19BHH2F: Contains Phox1 homeodomain (amino acids 43 to 150) fused in frame to the epitope tag in pl9BHA followed by ZBP zinc fingers 6 and 7 (amino acids 328 to 410). An XbaI-BamHI fragment from p19B2F containing sequences encoding ZBP zinc fingers 6 and 7 was ligated between the SpeI and BamHI sites of p19BHH.

p19BHH4F: Contains Phox1 homeodomain (amino acids 43 to 150) fused in frame to the epitope tag in p19BHA followed by ZBP zinc fingers 4, 5, 6 and 7 (amino acids 300 to 410). An XbaI-BamHI fragment from p19B4F containing sequences encoding ZBP zinc fingers 4, 5, 6 and 7 was ligated between the SpeI and BamHI sites of p19BHH.

p19BHH7F: Contains Phox1 homeodomain (amino adds 43 to 150) fused in frame to the epitope tag in p19BHA followed by ZBP zinc fingers 1 to 7 (amino acids 216 to 410). An XbaI-BamHI fragment from p19B7F containing sequences encoding ZBP zinc fingers 1 to 7 was ligated between the SpeI and BamHI sites of p19BHH.

p19BHHZF1: Contains Phox1 homeodompin (amino acids 43 to 150) fused in frame to the epitope tag in p19BHA followed by ZBP zinc finger 1 (amino acids 204 to 241). An XbaI-BamHI fragment from p19BZF1 containing sequences encoding ZBP zinc finger 1 was ligated between the SpeI and BamHI sites of p19BHH.

p019BHHZF123:Contains Phox1 homeodomain (amino acids 43 to 150) fused in frame to the epitope tag in p19BHA followed by ZBP zinc fingers 1, 2 and 3 (amino acids 204 to 297). An XbaI-BamHI fragment from p19BZF123 containing sequences encoding ZBP zinc fingers 1, 2 and 3 was ligated between the SpeI and BamHI sites of p19BHH.

PCR Primers:

SRE-ZBP

2F-Xba5':
5'-TCAGTCTAGATGTAACATATGCCAGAAAGCCTTC-3' (SEQ ID NO. 66)

4F-Xba5':
5'-TCAGTCTAGATGCAAGGAGTGTGGAAAAACCTTT-3' (SEQ ID NO. 67)

7F-Xba5':
5'-TCAGTCTAGATGTCATGAGTGTGGGAAAGCCTTT-3' (SEQ ID NO. 68)

ZNF-Spe/Bam:
5'-TCAGGGATCCTCAATAACTAGTAGCCAGTTTGTCTTTGTGGTGATA-3' (SEQ ID NO. 69)

ZBPZF15':
5'-TCAGTCTAGACATAAGAAAGTCCTCTCTAG-3' (SEQ ID NO. 70)

ZBPZF13':
5'-TCAGGGATCCTCTATATCAACTAGTAGGCTTCTCACCAAGATGG-3' (SEQ ID NO. 71)

ZBPZF33':
5'-TCAGGGATCCTCTATATCAACTAGTGGGCTCCTCCTGACTGTG-3' (SEQ ID NO. 72)

PHOX1

Phox HH 5' Primer:
5'-TCAGTCTAGAGGCCGGAGCCTGCTGGAGT-3' (SEQ ID NO. 73)

Phox HH Spe/Bam:
5'-TCAGGGATCCTCAATAACTAGTGTAGGATTTGAGGAGGGAA-3' (SEQ ID NO. 74)

EQUIVALENTS

The invention disclosed herein is of broad applicability and is susceptible to many useful variations within the context described and illustrated herein. Those skilled in the art will recognize or be able to ascertain from the foregoing disclosoure, using no more than routine experimentation, many valuable equivalents to the specific embodiments of the invention described herein. Such equivalents are intended to be encompassed by the following claims.

pCGNN ZFHD1-FKBPX3, ATCC 97399, was deposited with the American Type Culture Collection, 10801 University Boulevard, Manassas, Virginia 20110-2209 on December 28, 1995.

The invention claimed is:

1. A nucleic acid encoding a chimeric protein comprising a composite nucleic acid-binding region, wherein the composite nucleic acid-binding region comprises
   (a) at least two nucleic acid-binding domains, each of which binds a portion of the composite binding site, and wherein at least two of these nucleic acid-binding domains
      (i) do not occur in the same protein in nature;
      (ii) do not occur in the same protein in the order in which they are present in the chimeric protein; or
      (iii) do not occur in nature with the same spacing that is present in the chimeric protein, and
   (b) at least one additional domain, distinct from said nucleic acid-binding domains, which binds to a ligand and mediates formation of protein-protein complexes in a ligand-dependent manner.

2. A nucleic acid of claim 1 which encodes a chimeric protein comprising a composite DNA-binding region containing a homeodomain convalently linked to at least one zinc finger domain.

3. A eukaryotic expression construct comprising a nucleic acid encoding a transcription activating factor of claim 2 operably linked to at least one expression control element permitting gene expression in eukaryotic cells.

4. A nucleic acid of claim 1 which encodes a chimeric protein comprising the peptide sequence of ZFHD1.

5. A eukaryotic expression construct comprising a nucleic acid of claim 4 encoding a transcription activating factor operably linked to at least one expression control element permitting gene expression in eukaryotic cells.

6. A nucleic acid of claim 1 which encodes a chimeric protein further comprising a transcription activation domain.

7. A eukaryotic expression construct comprising a nucleic acid of claim 6 encoding a transcription activating factor operably linked to at least one expression control element permitting gene expression in eukaryotic cells.

8. A eukaryotic expression construct of claim 3, 5, or 7 wherein at least one expression control element includes an inducible promoter permitting regulated expression of the nucleic acid encoding the chimeric protein.

9. A method for genetically engineering cells to express a chimeric protein comprising a composite nucleic acid-binding region, wherein the composite nucleic acid-binding region comprises
   (a) at least two nucleic acid-binding domains, each of which binds a sequence which is a portion of the composite binding site, and wherein at least two of these nucleic acid-binding domains
      (i) do not occur in the same protein in nature;
      (ii) do not occur in the same protein in the order in which they are present in the chimeric protein; or
      (iii) do not occur in nature with the same spacing that is present in the chimeric protein, and
   (b) at least one additional domain, distinct from said nucleic acid-binding domains, which binds to a ligand and mediates formation of protein-protein complexes in a ligand-dependent manner
comprising the steps of:
   (a) providing an expression construct of claim 3, 5, or 7 for directing the expression in a eukaryotic cell of a chimeric protein which is capable of binding to a DNA sequence linked to a target gene, and,
   (b) introducing the expression construct into cells in a manner permitting expression of the introduced DNA in at least a portion of the cells.

10. A method of claim 9 wherein the target gene and the DNA sequence linked thereto are endogenous to the cells.

11. A method of claim 9 which flier comprises the step of introducing into the cells a nucleic acid containing a target gene and the DNA sequence to which the chimeric protein is capable of binding.

12. A method of claim 11 wherein the chimeric protein is a transcription factor capable of binding to a DNA sequence linked to the target gene and repressing transcription of the target gene.

13. A method of claim 9 in which the cells into which the expression construct is introduced are maintained in culture.

14. A method of claim 9 in which the cells are present within an organism.

15. A method of claim 9 wherein the chimeric protein is a transcription factor capable of binding to a DNA sequence linked to the target gene and activating transcription of the target gene.

16. A method of claim 9 wherein the chimeric protein is capable of binding to a DNA sequence and cleaving DNA linked to that sequence.

17. A nucleic acid of claim 1 which encodes a chimeric protein further comprising a transcription repression domain.

18. A nucleic acid of claim 1 which encodes a chimeric protein further comprising a domain capable of cleaving DNA.

19. A genetically engineered cell containing and capable of expressing a nucleic acid of claim 18.

20. A non-human organism containing genetically engineered cells of claim 6, 17, or 18.

21. A eukaryotic expression construct comprising a nucleic acid of claim 1 operably linked to at least one expression control element permitting gene expression in eukaryotic cells.

22. A gentically engineered cell containing and capable of expressing a nucleic acid of claim 1.

23. A genetically engineered cell of claim 22 which further contain a DNA sequence to which the encoded chimeric protein is capable of binding.

24. A genetically engineered cell of claim 22 in which the chimeric protein activates the transcription of a gene linked to a DNA sequence to which the chimeric protein binds.

25. A genetically engineered cell of claim 22 in which the chimeric protein represses the transcription of a gene linked to a DNA sequence to which the chimeric protein binds.

26. A method of repressing the expression of a target gene in a cell comprising the steps of:
  (a) providing a genetically engineered cell of claim 22 containing and capable of expressing a first DNA sequence encoding a chimeric protein which is capable of
    (i) binding to a second DNA sequence linked to a target gene of interest also present within the cell, and
    (ii) repressing the transcription of the target gene; and,
  (b) maintaining the cell under conditions permitting gene expression and protein production.

27. A method of cleaving a target DNA sequence in a cell comprising the steps of:
  (a) providing a genetically engineered cell of claim 22 containing and capable of expressing a first DNA sequence encoding a chimeric protein which is capable of
    (i) binding to a second DNA sequence linked to a target DNA sequence also present within the cell, and
    (ii) cleaving the target DNA sequence; and,
  (b) maintaining the cell under conditions permitting gene expression and protein production.

28. A method of claim 20, 3 or 5, wherein expression of the first DNA sequence is controlled by an inducible promoter, and the conditions permitting gene expression and protein production permit expression of the first DNA sequence.

29. A genetically engineered cell of claim 22, comprising and capable of expressing a DNA sequence encoding a chimeric protein comprising at least one homoedomain.

30. A genetically engineered cell of claim 22, comprising and capable of expressing a DNA sequence encoding a chimeric protein comprising at least one zinc finger domain.

31. A genetically engineered cell of claim 22, comprising and capable of expressing a DNA sequence encoding a chimeric protein comprising at least three nucleic acid-binding domains, each of which binds a sequence which is a portion of the composite binding site.

32. A genetically engineered cell of claim 22, comprising and capable of expressing a DNA sequence encoding a chimeric protein comprising at least one ligand-binding domain which binds to a selected ligand, which ligand further binds to the ligand-binding domain of another protein to form a ligand cross-linked complex including the chimeric protein and the other protein, and which ligand has one or more of the following characteristics:
  (i) the ligand is not a protein; and
  (ii) the ligand has a molecular weight less than 5 kD.

33. A genetically engineered cell of claim 22, comprising and capable of expressing a DNA sequence, which encodes a chimeric protein comprising two or more ligand-binding domains.

34. A genetically engineered cell of claim 22, comprising and capable of expressing a DNA sequence, which encodes a chimeric protein comprising at least one ligand-binding domain which binds to a ligand having a molecular weight less than 2 kD.

35. A genetically engineered cell of claim 22, comprising and capable of expressing a DNA sequence, which encodes a chimeric protein comprising at least one naturally-occurring ligand-binding domain.

36. A genetically engineered cell of claim 22, comprising and capable of expressing a DNA sequence, which encodes a chimeric protein comprising at least one ligand-binding domain comprising a non-naturally-occurring peptide sequence.

37. A genetically engineered cell of claim 22, comprising and capable of expressing a DNA sequence, which encodes a chimeric protein which binds to the selected ligand with a kD value less than or equal to about $10^{-6}$M.

38. A genetically engineered cell of claim 22, comprising and capable of expressing a DNA sequence, which encodes a chimeric protein which binds to the selected ligand with a kD value less than or equal to about $10^{-8}$M.

39. A genetically engineered cell of claim 22, comprising and capable of expressing a DNA sequence, which encodes a chimeric protein comprising at least one ligand-binding domain comprising an immunophilin domain, cyclophilin domain, or steroid binding domain.

40. A genetically engineered cell of claim 22, comprising and capable of expressing a DNA sequence, which encodes a chimeric protein comprising at least one FKBP domain.

41. A genetically engineered cell of claim 22, comprising and capable of expressing a DNA sequence, which encodes a chimeric protein comprising at least one FRB region of a FRAP protein.

42. A genetically engineered cell of claim 22, comprising and capable of expressing a DNA sequence, which encodes a chimeric protein comprising at least one ligand-binding domain which binds to FK506, rapamycin, or a derivative thereof.

43. A genetically engineered cell of claim 22, comprising and capable of expressing a DNA sequence, which encodes a chimeric protein which further comprises a nuclear localization domain.

44. A method of expressing a target gene in a cell comprising the steps of:
  (a) providing a gentically engineered cell containing a nucleic acid of claim 1, and a target gene having a transcriptional regulatory sequence including the composite nucleic acid-binding region; and
  (b) maintaining the cell under conditions permitting gene expression and protein production.

45. A nucleic acid of claim 1 encoding a chimeric protein comprising at least one homoedomain.

46. A nucleic acid of claim 1 encoding a chimeric protein comprising at least one zinc finger domain.

47. A nucleic acid of claim 1 encoding a chimeric protein comprising at least three nucleic acid-binding domains, each of which binds a sequence which is a portion of the composite binding site.

48. A nucleic acid of claim 1 encoding a chimeric protein comprising at least one ligand-binding domain which binds to a selected ligand, which ligand further binds to the ligand-binding domain of another protein to form a ligand cross-linked complex including the chimeric protein and the other protein, and which ligand has one or more of the following characteristics:
  (i) the ligand is not a protein; and
  (ii) the ligand has a molecular weight less than 5 kD.

49. A nucleic acid of claim 1, which encodes a chimeric protein comprising two or more ligand-binding domains.

50. A nucleic acid of claim 1, which encodes a chimeric protein comprising two or more different ligand-binding domains.

51. A nucleic acid of claim 1, which encodes a chimeric protein comprising at least one ligand-binding domain which binds to a ligand having a molecular weight less than 2 kD.

52. A nucleic acid of claim 1, which encodes a chimeric protein comprising at least one naturally-occurring ligand-binding domain.

53. A nucleic acid of claim 1, which encodes a chimeric protein comprising at least one ligand-binding domain comprising a non-naturally-occurring peptide sequence.

54. A nucleic acid of claim 1, which encodes a chimeric protein which binds to the selected ligand with a kD value less than or equal to about $10^{-6}$M.

55. A nucleic acid of claim 1, which encodes a chimeric protein which binds to the selected ligand with a kD value less than or equal to about $10^{-8}$M.

56. A nucleic acid of claim 1, which encodes a chimeric protein comprising at least one ligand-binding domain comprising an immunophilin domain, cyclophilin domain, or steroid binding domain.

57. A nucleic acid of claim 1, which encodes a chimeric protein comprising at least one FKBP domain.

58. A nucleic acid of claim 1, which encodes a chimeric protein comprising at least one FRB region of a FRAP protein.

59. A nucleic acid of claim 1, which encodes a chimeric protein comprising at least one ligand-binding domain which binds to FK506, rapamycin, or a derivative thereof.

60. A nucleic acid of claim 1, wherein the chimeric protein further comprises a nuclear localization domain.

* * * * *